(12) United States Patent
Foreman et al.

(10) Patent No.: US 7,951,061 B2
(45) Date of Patent: *May 31, 2011

(54) DEVICES FOR TARGETED DELIVERY OF THERMOTHERAPY, AND METHODS RELATED THERETO

(76) Inventors: Allan Foreman, Epping, NH (US); Wolfgang Daum, Groton, MA (US)

( * ) Notice: Subject to any disclaimer, the term of this patent is extended or adjusted under 35 U.S.C. 154(b) by 1389 days.

This patent is subject to a terminal disclaimer.

(21) Appl. No.: 11/258,598

(22) Filed: Oct. 25, 2005

(65) Prior Publication Data
US 2006/0142748 A1    Jun. 29, 2006

Related U.S. Application Data

(63) Continuation-in-part of application No. 10/176,950, filed on Jun. 18, 2002, now Pat. No. 7,074,175.

(60) Provisional application No. 60/307,785, filed on Jul. 25, 2001.

(51) Int. Cl.
*A61N 2/00* (2006.01)
(52) U.S. Cl. .......................................................... 600/9
(58) Field of Classification Search ................. 600/9–15; 607/103, 105; 977/DIG. 1, 902, 904, 905, 977/911, 912
See application file for complete search history.

(56) References Cited

U.S. PATENT DOCUMENTS

| | | |
|---|---|---|
| 4,106,488 A | 8/1978 | Gordon |
| 4,303,636 A | 12/1981 | Gordon |
| 4,312,364 A | 1/1982 | Convert |
| 4,323,056 A | 4/1982 | Borrelli |
| 4,392,040 A | 7/1983 | Rand |
| 4,452,773 A | 6/1984 | Molday |
| 4,454,234 A | 6/1984 | Czerlinski |
| 4,545,368 A | 10/1985 | Rand et al. |
| RE32,066 E | 1/1986 | Leveen |
| 4,569,836 A | 2/1986 | Gordon |
| 4,574,782 A | 3/1986 | Borrelli |
| 4,590,922 A | 5/1986 | Gordon |
| 4,610,241 A | 9/1986 | Gordon |
| 4,622,952 A | 11/1986 | Gordon |
| 4,662,359 A | 5/1987 | Gordon |
| 4,678,667 A | 7/1987 | Meares |
| 4,708,718 A | 11/1987 | Daniels |
| 4,735,796 A | 4/1988 | Gordon |
| 4,753,894 A | 6/1988 | Frankel |

(Continued)

FOREIGN PATENT DOCUMENTS
DE        10156790        6/2003
(Continued)

OTHER PUBLICATIONS

Ivkov et al., Application of High Amplitude Alternating Magnetic Fields for Heat Induction of Nanoparticles Localized in Cancer, 2005, Clin. Can. Res. 11(19Suppl):7093s-7103s.

(Continued)

*Primary Examiner* — John P Lacyk

(57) ABSTRACT

Disclosed are devices for targeted delivery of thermotherapy. These devices are useful in the treatment of diseased tissue in conjunction with magnetic compositions. Further disclosed are methods for treating diseased tissue, which involve the administration of a thermotherapeutic magnetic composition to a patient or a portion of a patient, and the application of an alternating magnetic field to inductively heat the thermotherapeutic magnetic composition. The devices and the methods disclosed herein are useful for the treatment of a variety of indications, such as cancer, diseases of the immune system, pathogen-borne diseases, hormone-related diseases, non-cancerous diseased cells or tissue, and undesirable matter, such as toxins and reaction-by-products associated with organ transplants.

92 Claims, 10 Drawing Sheets

U.S. PATENT DOCUMENTS

| | | | |
|---|---|---|---|
| 4,758,429 | A | 7/1988 | Gordon |
| 4,767,611 | A | 8/1988 | Gordon |
| 4,813,399 | A | 3/1989 | Gordon |
| 4,889,120 | A | 12/1989 | Gordon |
| 4,923,437 | A | 5/1990 | Gordon |
| 4,950,221 | A | 8/1990 | Gordon |
| 4,979,518 | A | 12/1990 | Itoh |
| 4,983,159 | A | 1/1991 | Rand |
| 4,996,991 | A | 3/1991 | Gordon |
| 5,043,101 | A | 8/1991 | Gordon |
| 5,067,952 | A | 11/1991 | Gudov et al. |
| 5,087,438 | A | 2/1992 | Gordon |
| 5,099,756 | A | 3/1992 | Franconi |
| 5,128,147 | A | 7/1992 | Leveen |
| 5,169,774 | A | 12/1992 | Frankel |
| 5,203,782 | A | 4/1993 | Gudov |
| 5,300,750 | A | 4/1994 | Carter, Jr. et al. |
| 5,411,730 | A | 5/1995 | Kirpotin |
| 5,429,583 | A | 7/1995 | Paulus |
| 5,441,746 | A | 8/1995 | Chagnon |
| 5,468,210 | A | 11/1995 | Matsui |
| 5,506,343 | A | 4/1996 | Kufe |
| 5,547,682 | A | 8/1996 | Chagnon |
| 5,612,019 | A | 3/1997 | Gordon |
| 5,620,480 | A | 4/1997 | Rudie |
| 5,622,686 | A | 4/1997 | Gordon |
| 5,629,197 | A | 5/1997 | Ring |
| 5,658,234 | A | 8/1997 | Dunlavy |
| 5,677,171 | A | 10/1997 | Hudziak |
| 5,693,763 | A | 12/1997 | Codington |
| 5,705,157 | A | 1/1998 | Greene |
| 5,720,954 | A | 2/1998 | Hudziak |
| 5,772,997 | A | 6/1998 | Hudziak |
| 5,859,206 | A | 1/1999 | Vandlen |
| 5,891,996 | A | 4/1999 | Mateo de Acosta del Rio |
| 5,916,539 | A | 6/1999 | Pilgrimm |
| 5,922,845 | A | 7/1999 | Deo |
| 5,935,866 | A | 8/1999 | Chagnon |
| 5,958,374 | A | 9/1999 | Meares |
| 5,968,511 | A | 10/1999 | Akita |
| 6,008,203 | A | 12/1999 | Magnani |
| 6,015,567 | A | 1/2000 | Hudziak |
| 6,037,129 | A | 3/2000 | Cole |
| 6,054,561 | A | 4/2000 | Ring |
| 6,074,337 | A | 6/2000 | Tucker |
| 6,149,576 | A | 11/2000 | Gray |
| 6,165,440 | A | 12/2000 | Esenaliev |
| 6,165,464 | A | 12/2000 | Hudziak |
| 6,167,313 | A | 12/2000 | Gray |
| 6,190,870 | B1 | 2/2001 | Schmitz |
| 6,242,196 | B1 | 6/2001 | Spiegelman |
| 6,252,050 | B1 | 6/2001 | Ashkenazi |
| 6,281,202 | B1 | 8/2001 | Magnani |
| 6,303,755 | B1 | 10/2001 | Deo |
| 6,344,203 | B1 | 2/2002 | Sandrin |
| 6,347,633 | B1 | 2/2002 | Groth |
| 6,387,371 | B1 | 5/2002 | Hudziak |
| 6,387,888 | B1 | 5/2002 | Mincheff |
| 6,391,026 | B1 | 5/2002 | Hung |
| 6,470,220 | B1 | 10/2002 | Kraus, Jr. et al. |
| 6,514,481 | B1 | 2/2003 | Prasad et al. |
| 6,541,039 | B1 | 4/2003 | Lesniak et al. |
| 6,565,887 | B1 | 5/2003 | Gray et al. |
| 6,575,893 | B2 | 6/2003 | Feucht |
| 6,599,234 | B1 | 7/2003 | Gray et al. |
| 6,638,494 | B1 | 10/2003 | Pilgrimm |
| 6,669,623 | B1 | 12/2003 | Jordan |
| 2001/0011151 | A1 | 8/2001 | Feucht |
| 2001/0012912 | A1 | 8/2001 | Feucht |
| 2002/0052594 | A1 | 5/2002 | Goldenberg |
| 2002/0125975 | A1 | 9/2002 | Feucht |
| 2003/0028071 | A1 | 2/2003 | Handy |
| 2003/0092029 | A1 | 5/2003 | Josephson et al. |
| 2003/0180370 | A1 | 9/2003 | Lesniak et al. |
| 2005/0249817 | A1 | 11/2005 | Haik et al. |
| 2006/0142749 | A1 | 6/2006 | Ivkov |
| 2006/0147380 | A1 | 7/2006 | Lanza et al. |

FOREIGN PATENT DOCUMENTS

| | | |
|---|---|---|
| EP | 0040512 | 11/1981 |
| EP | 0913167 | 5/1999 |
| EP | 0673255 B1 | 8/2001 |
| EP | 00344270 B1 | 11/2004 |
| JP | 1244767 | 9/1989 |
| JP | 11197257 | 9/1989 |
| JP | 2004/105722 A | 4/2004 |
| WO | WO 9411023 A1 | 5/1994 |
| WO | WO 97/43005 A1 | 11/1997 |
| WO | WO 99/19000 A1 | 4/1999 |
| WO | WO 00/52714 A1 | 9/2000 |
| WO | WO 03/047633 A2 | 6/2003 |

OTHER PUBLICATIONS

Denardo et al., Development of Tumor Targeting Bioprones ($^{111}$In-Chimeric L6 Monoclonal Antibody Nanoparticles) for Alternating Magnetic Field Cancer Therapy, 2005, Clin. Can. Res. 11(19 Suppl.):7087s-7092s.

Peasley, Destruction of human immunodeficiency-infected cells by ferrofluid particles manipulated by an external magnetic field: mechanical disruption and selective introduction of cytotoxic or antiretroviral substances into target cells, 1996, Medical Hypotheses, 46: 5-12, No. 1 England (Abstract).

Torchilin et al., Magnetic sephadex as a carrier for enzyme immobilization and drug targeting, 1985, J of Biomedical Materials Res. 19: 461-466, No. 4 United States (Abstract).

Molina et al., Trastuzumab (herceptin), a humanized anti-Her2 receptor monoclonal antibody, inhibits basal and activated Her2 ectodomain cleavage in breast cancer cells, 2001, Cancer Research Jun. 15, 61(12) 4744-4749 (Abstract).

Wong et al., Human scFv antibody fragments specific for the epithelial tumour marker MUC-1, selected by phage display on living cells, 2001, Cancer Immunol. Immunother, Apr.; 50(2): 93-101 (Abstract).

Winthrop et al., Development of a hyperimmune anti-MUC-1 single chain antibody fragment phage display library for targeting breast cancer, 1999, Clin Can Research Oct; 5(10 suppl.): 3088-3094.

Richman et al., Systemic radiotherapy in metastatic breast cancer using 90Y-linked monoclonal MUC-1 antibodies, 2001, Crit Rev Oncol Hematol 38: 25-35, Ireland (Abstract).

Kobayashi et al., Targeting hyperthermia for renal cell carcinoma using human MN antigen-specific magnetoliposomes, 2001, Japanese J. of Cancer Res. 92: No. 10 (Abstract).

Young et al., A pulsed power supply system for producing high intensity magnetic and electric fields for medical applications, IEEE Conference Record-Abstracts, PPPS-2001 Pulsed Power Plasma Science 2001, 28th IEEE International Conference on Plasma Science and 13th IEEE International Pulsed Power Conference (Cat. No. 0ICH37255) 2001, pp. 322, USA (Abstract).

Peterson et al.., Effect of multiple, repeated doses of radioimmunotherapy on target antigen expression (breast MUC-1 mucin in breast carcinomas, 1997, Cancer Res. 57(6): 1103-1108 (Abstract).

Diaz et al., Expression of epithelial mucins Muc1, Muc2, and Muc3 in ductal carcinoma in situ of the breast, 2001, Breast J. 7(1): 40-45 (Abstract).

Barratt-Boyles, Making the most of mucin: a novel target for tumor immunotherapy, 1996, Cancer Immunol. Immunother. 43(3): 142-151.

Menard et al., Role of Her2 gene overexpression in breast carcinoma, 2000, J. Cell Physiol. 182(2): 150-162 (Abstract).

Hadden, The immunology and immunotherapy of breast cancer: an update, 1999, Int. J. Immunopharacol., 21(2): 79-101 (Abstract).

Tucker et al., Defining the heating characteristics of ferromagnetic implants using calorimetry, 2000, J. of Biomedical Materials Research 53: 791-798 (Abstract).

Takegami et al., New ferromagnetic bone cement for local hyperthermia, 1998, J. Biomedical Materials Research 43: 210-214 (Abstract).

Paulus et al., Corrosion analysis of NiCu and PdCo thermal seed alloys used as interstitial hyperthermia implants, 1997, vol. 18: 1609-1614 (Abstract).

Graef, Materials for low Curie temperature induction hearing of tumors (Hyperthermia), 1991, Ph.D. Dissertation, University of Arizona (Abstract).

Petrarca et al., Isolation of MUCI-primed B lymphocytes from tumour-draining lymph nodes by immonomagnetic beads, 1999, Cancer Immunology Immunotherapy 47 No. 5: 272-277 (Abstract).

Shinkai et al., Targeting hyperthermia for renal cell carcinoma using human mn antigen-specific magnetoliposomes, 2001, Jpn. J. Cancer Res. 92: 1138-1145 (Abstract).

Suzuki et al., Preparation and characteristics of magnetite-labelled antibody with the use of poly(ethylene glycol) derivatives, 1995, Biotechnol. Appl. Biochem. 21: 335-345.

Shinkai et al., Antibody-conjugated magnetoliposomes for targeting cancer cells and their application in hyperthermia, 1994, Biotechnol. Appl. Biochem. 21: 125-137.

Jordan et al., Magnetic fluid hyperthermia (MFH): Cancer treatment with AC magnetic field induced excitation of biocompatible superparamagnetic nanoparticles, 1999, J. Magnetism and Magnetic Materials, 201: 413-419.

Jordan et al., Inductive heating of ferromagnetic particles and magnetic fluids: physical evaluation of their potential for hyperthermia, 1993, Int. J. Hyperthermia 9: 51-68.

Jordan et al., Magnetic Fluid Hyperthermia (MFH) in Scientific and Clinical Applications of Magnetic Carriers, Hafeli et al., ed, 1997, 569-595 USA.

Chan et al., Synthesis and evaluation of colloidal magnetic iron oxides for the site-specific radiofrequency-induced hyperthermia of cancer, 1993, J. Magnetism and Magnetic Materials, 122: 374-378, Holland.

Brusentsov et al., Evaluation of ferromagnetic fluids and suspensions for the site-specific radiofrequency-induced hyperthermia of MX11 sarcoma cells in vitro, 2001, J. Magnetism and Magnetic Materials, 225: 113-117.

Jones et al., Experimental examination of a targeted hyperthermia system using inductively heated ferromagnetic microspheres in rabbit kidney, 2001, Physics in Medicine and Biology 46: 385-398.

Jones et al., Evaluation of ferromagnetic materials for low-frequency hysteresis heating of tumors, 1992, Physics in Medicine and Biology 37: 293-299.

Moroz et al., Targeting liver tumors with hyperthermia: Ferromagnetic embolization in a rabbit liver tumor model, 2001, J. of Surgical Oncology 78: 22-29.

Hiergeist et al., Application of magnetic ferrofluids for hyperthermia, 1999, J. Magnetism and Magnetic Materials 201: 420-422.

Shinkai et al., Intracellular hyperthermia for cancer using magnetite cationic liposomes: In vitro study, Jpn, 1996, J. Cancer Research 87: 1179-1183.

Carter, Improving the efficacy of antibody-based cancer therapies, 2001, Nature Reviews 1: 118-129.

McDevitt et al., Tumor Therapy with targeted atomic nanogenerators, 2001, Science, 294: 1537-1550.

Segal et al., Introduction: bispecific antibodies, 2001, J. Immunol. Methods, 248: 1-6.

Reiter et al., Recombinant immunotoxins in targeted cancer cell therapy, 2001, Adv. Can. Res. pp. 93-124.

Hergt et al., Physical limits of hyperthermia using magnetite fine particles, 1998, IEEE Trans. On Mag., 34: 3745-3754.

Hynynen et al., State of the art in medicine: Hyperthermia in cancer treatment, 1990, Investigative Radiology, 2: 824-834.

Jordan et al.., Cellular uptake of magnetic fluid particles and their effects on human adenocarcinoma cells exposed to AC magnetic fields in vitro, 1996, Int. J. Hyperthermia 12: 705-722.

Chan et al.., Physical chemistry and in vivo tissue heating properties of colloidal magnetic iron oxides with increased power adsorption rates in Scientific and Clinical Applications of Magnetic Carriers, Hafeli et al. eds., 1997, pp. 607-618, Plenum Press, New York, USA.

Suzuki et al.., Studies on liposomal ferromagnetic particles and a technique of high frequency inductive heating, Jpn, 1990, J. Soc. Cancer Ther., 25: 2649-2658.

Gordon et al., Intracellular hyperthermia: a biophysical approach to cancer treatment via intracellular temperature and biophysical alterations, 1979, Medical Hypothesis 5: 83-102.

Goldin et al.., The effects of diapulse on the healing of wounds: a double-blind randomized controlled trial in man, 1981, Brit. J. of Plastic Surgery 34: 267-270.

Gilchrist et al., Selective inductive heating of lymph nodes, 1957, Annals of Surgery 146: 596-606.

Luderer et al., Glass-ceramic-mediated, magnetic-field-induced localized hyperthermia: Response of a murine mammary carcinoma, 1983, Radiation Research 94: 190-198.

Bartlett et al., On the use of ferromagnetic microparticles in microwave and radio frequency hyperthermia, 1988, J. of the Inst. of Electronic and Radio Engineers 58: 197-201.

Bacri et al., Use of magnetic nanoparticles for thermolysis of cells in a ferrofluid, 1997, Scientific and Clinical Applications of Magnetic Carriers, Hafeli et al., eds., pp. 597-606, Plenum Press, New York, USA.

Mitsumori et al., Targeted hyperthermia using dextran magnetite complex: A new treatment modality for liver tumors, 1996, Hepato-Gastroenterology, 43: 1431-1437.

Borelli et al.., Hysteresis heating for the treatment of tumours, 1984, Phys Med Biol. 29 No. 5: 487-494, England.

Mitsumori et al., Development of intra-arterial hyperthermia using a dextran-magnetite complex, 1994, Int. J. Hyperthermia 10: 785-793.

Csuka et al., Prognostic factors of breast cancer, 2000, Magy. Onkol 44: 53-60 (Abstract).

Luftner et al., Nuclear matrix proteins as biomarkers for breast cancer, 2002, Expert Rev. Mol. Diag. 2: 23-3 (Abstract).

Krishnamurthy et al., Molecular and biologic markers of premalignant lesions of human breast, 2002, Adv. Mat. Pathol. 9: 185-197 (Abstract).

Palmu et al., Expression of C-KIT and HER-2 tyrosine kinase receptors in poor-prognosis breast cancer, 2002, Anticancer Res. 22: 411-414 (Abstract).

Esteva et al., Expression of erbB/HER receptors, heregulin and P38 in primary breast cancer using quantitative immunohistochemistry, 2002, Pathol. Oncol. Res. 7: 171-177 (Abstract).

O'Hanlon et al., An immunohistochemical study of p21 and p53 expression in primary node-positive breast carcinoma, 2002, Eur. J. Surg. Oncol. 28: 103-107 (Abstract).

Aguilar et al., The transmembrane heregulin precursor is functionally active, 2001, J. Biol. Chem. 276: 44099-44107 (Abstract).

Defazio et al., Expression of c-erbB receptors, heregulin and estrogen receptor in human breast cell lines, 2000, Int. J. Cancer 87: 487-498 (Abstract).

Hadden, The immunology and immunotherapy of breast cancer: an update, 1999, Int. J. Immunopharmacol. 21: 79-101 (Abstract).

Gion et al., CA27.29: a valuable marker for breast cancer management. A confirmatory multicentric study on 603 cases, 2001, Eur. J. Cancer 37: 355-363 (Abstract).

Suo et al., EGFR family expression in breast carcinomas. C-erbB-2 and c-erbB-4 receptors have different effects on survival, 2002, J. Pathol. 196: 17-25 (Abstract).

Parker et al., E-cadherin as a prognostic indicator in primary breast cancer, Br. J. Cancer 85: 1958-1963 (Abstract).

Lakhani et al., The pathology of familial breast cancer: predictive value of immunohistochemical markers estrogen receptor, progesterone receptor, HER-2, and p53 in patients with mutations in BRCA1 and BRCA2, 2002, J. Clin. Oncol. 20: 2310-2318 (Abstract).

Moritani et al., Availability of CD10 immunohistochemistry as a marker of breast myoepithelial cells on paraffin sections, 2002, Mod. Pathol. 15: 397-405 (Abstract).

Spizzo et al., Prognostic significance of Ep-CAM and Her-2/neu Overexpression in invasive breast cancer, 2002, Int. J. Cancer 98: 883-888 (Abstract).

Opezzo et al., Production and functional characterization of two mouse/human chimeric antibodies with specificity for the tumor associated Tn antigen, 2000, Hibridoma 19: 229-239 (Abstract).

Babino et al., Tn antigen is a pre-cancerous biomarker in breast tissue and serum in n-nitrosomethylurea-induced rat carcinogenesis, 2000, Int. J. Cancer 86: 753-759 (Abstract).

Lapetti et al., Controlling tumor-derived and vascular endothelial cell growth: role of the 4Ff2 cell surface antigen, 2001, Am. J. Pathol. 159: 165-178 (Abstract).

Molina et al., Tastuzumab (herceptin), a humanized anti-Her2 receptor monoclonal antibody, inhibits basal and activated Her2 ectodomain cleavage in breast cancer cells, 2001, Cancer Res. 61: 4744-4749 (Abstract).

Wong et al., Human scFv antibody fragments specific for the epithelial tumor marker MUC-1, selected by phage display on living cells, 2001, Cancel Immunol. Immunother. 50::93-101 (Abstract).

Isaacs et al., Humanized monoclonal antibody therapy for rheumatoid arthritis, 1992, Lancet 240:748-752 (Abstract).

Isaacs et al., Humanized anti-CD4 monoclonal antibody therapy of autoimmune and inflammatory disease, 1997, Clin. Exp. Immunol, 110: 158-166 (Abstract).

Coles et al., Pulsed monoclonal antibody treatment and autoimmune thyroid disease in multiple sclerosis, 1999, Lancet 354: 1691-1695 (Abstract).

Moseley et al., HMFGI antigen: a new marker for carcinomatous meningitis, 1989, Int. J. Cancer 44: 440-444 (Abstract).

Stockhammer et al., Vascular endothelial growth factor in CSF: a biological marker for carcinomatous meningitis, 2000, Neurology: 54: 1670-1676 (Abstract).

Gourevitch et al., Polymorphic epithelial mucin (MUC-1)-containing circulating immune complexes in carcinoma patients, 1995, Br. J. Cancer 72: 934-938 (Abstract).

Ramakrishna et al., Generation and phenotypic characterization of new human ovarian cancer cell lines with the identification of antigens potentially recognizable by HLA-restricted cytotoxic T cells, 1997, Int. J. Cancer 73: 143-150 (Abstract).

Snijdewint et al., Cellular and humoral immune responses to MUC1 mucin tandem-repeat peptides in ovarian cancer patients and controls, 1999, Cancer Immunol. Immunother. 48: 47-55 (Abstract).

Wu et al., Activated matrix metalloproteinase-2-a potential marker of prognosis for epithelial ovarian cancer, 2002, Gynecol. Oncol. 84: 126-134 (Abstract).

Taylor et al., Shed membrane fragment-associated markers for endometrial and ovarian cancers, 2002, Gynecol. Oncol. 84: 443-448 (Abstract).

Davidson et al., Ovarian carcinoma and serous effusions. Changing views regarding tumor progression and review of current literature, 2001, Anal. Cell Pathol. 23: 107-128 (Abstract).

Jiang et al., Vaccination with a mixed vaccine of autogenous and allogenic breast cancer cells and tumor associated antigens CA15-3, CEA and CA125-results in immune and clinical responses in breast cancer patients, 2000, Cancer Biother. Radiopharm. 15: 495-505 (Abstract).

Garcia-Pachon et al., Diagnostic value of C-reactive protein in exudative pleural effusions, 2002, Eur. J. Intern. Med. 13: 246-249 (Abstract).

Ma et al., Molecular cloning and expression analysis of feline melanoma antigen (MAGE) obtained from a lymphoma cell line, 2001, Vet. Immunol. Immunopathol. 83: 241-252 (Abstract).

Barker et al., The MAGE proteins: emerging roles in cell cycle progression, apoptosis, and neurogenic disease, 2002, J. Neurosci. Res. 67: 705-712 (Abstract).

McTernan et al., Increased resistin gene and protein expression in human abdominal adipose tissue, 2002, J. Clin. Endocrinol. Metab. 87: 2407 (Abstract).

Xu et al., Altered tumor necrosis factor-alpha (TNF-alpha) processing in adipocytes and increased expression of transmembrane TNF-alpha in obesity, 2002, Diabetes 51: 1876-1883 (Abstract).

George et al., Functional inhibition of Ras by S-trans, trans-farnesyl thiosalicylic acid attenuates atherosclerosis in apolipoprotein E knockout mice, 2002, Circulation 105: 2416-2422 (Abstract).

Ibrahimi et al., Role of CD36 in membrane transport of long-chain fatty acids, 2002, Curr. Opin. Clin. Nutr. Metab. Care 5: 139-145 (Abstract).

Miyawaki et al., Inhibition of gastric inhibitory polypeptide signaling prevents obesity, 2002, Nat. Med. 8: 738-742 (Abstract).

Ivkov et al., "Application of high amplitude alternating magnetic fields for heat induction of nanoparticles localized in cancer", 2005, Clinical Cancer Research 11(19 Suppl):7093s-7103s.

DeNardo et al., "Development of tumor targeting bioprobes (I I I In-Chimeric L6 monoclonal antibody nanoparticles) for alternating magnetic field cancer therapy", 2005, Clinical Cancer Research 11(19 Suppl):7087s-7092s.

Gruttner et al., Synthesis and Antibody Conjugation of Magnetic Nanoparticles with Improved Specific Power Absorption Rates for Alternating Magnetic Field Cancer Therapy, 2007, J. Magnetism and Magnetic Materials 311:181-186 (Dec. 13, 2006-available online).

Van Poznak et al., Assessment of Molecular Markers of Clinical Sensitivity to Single-Agent Taxane Therapy for Metastatic Breast Cancer, May 1, 2002, J. Clin. Oncol., 20(9):2319-2326.

International Search Report for PCT/US02/23650, Apr. 22, 2003.

DEVICES FOR TARGETED DELIVERY OF THERMOTHERAPY, AND METHODS RELATED THERETO

CROSS REFERENCE TO RELATED APPLICATIONS

This is a Continuation-in-Part Application claiming the benefit of and priority to Non-Provisional patent application Ser. No. 10/176,950 filed on Jun. 18, 2002, and Provisional Patent Application No. 60/307,785, filed on Jul. 25, 2001, both of which are incorporated herein by reference.

TECHNICAL FIELD

The present invention relates generally to thermotherapy devices, more specifically, devices for use with magnetic material compositions, and thermotherapeutic methods related thereto.

BACKGROUND

Despite considerable research effort and some success, cancer is still the second leading cause of death in the United States, claiming more than 500,000 lives each year according to American Cancer Society estimates. Traditional treatments are either invasive or expose the patient to considerable toxicity with often only modest success. Early detection, a result of better diagnostic practices and technology has improved the prognosis for many patients. Nevertheless, some cancers defy currently available treatment options, despite these improvements. Of the many forms of cancer that still pose a medical challenge, prostate, breast, lung, and liver claim the vast majority of lives each year.

Conventional treatments for many cancers, both in late and early stages, typically include surgery followed by radiation and/or chemotherapy both of which carry with them damaging side effects and considerable patient discomfort. Neither is completely effective against recurrence. For these reasons, it was desirable to provide improved and alternative techniques for treating cancer, particularly less invasive techniques that result in minimum or no collateral damage, and effective locally within target sites of the diseased organs. It was also desirable to provide techniques capable of being performed in a single or multiple treatment session(s), with minimal toxicity to the patient, and which could be targeted to the diseased tissues without requiring significant operator skill and input.

One such alternative technique is immunotherapy, which is a rapidly expanding type of therapy used for treating a variety of human diseases, including cancer. The FDA has approved a number of antibody-based cancer therapeutics. The emergence of antibody therapies is made possible by important advances in antibody technologies. The ability to engineer antibodies, fragments, and peptides with altered properties such as antigen binding affinity, molecular architecture, specificity, and valence has enhanced their use in therapies. The advantages of antibody engineering have overcome the limitations of mouse monoclonal antibodies. Cancer immunotherapeutics have made use of advances in the chimerization and humanization of mouse antibodies to reduce immunogenic responses in humans. High affinity human antibodies have also been obtained from transgenic mice that contain many human immunoglobulin genes. In addition, phage display technology, ribosome display, and DNA shuffling have allowed for the discovery of antibody fragments and peptides that have the desirable properties of high affinity and low immunogenicity for use as targeting ligands. All of these advances have made it possible to design an immunotherapy that has a desired antigen binding affinity, specificity, and minimal immune response.

The field of cancer immunotherapy makes use of markers that are expressed or over-expressed on cancer cells in comparison to normal cells. The identification of such markers is ongoing and the choice of a ligand/marker combination is critical to the success of any immunotherapy. Immunotherapy has fallen into several classes: (1) antibodies themselves that target growth receptors, disrupt cytokine pathways, or induce complement or antibody-dependent cytotoxicity; (2) direct arming of an antibody with a toxin, a radionucleotide, or a cytokine; (3) indirect arming of an antibody by attachment to immunoliposomes used to deliver a toxin or by attachment to an immunological cell effector (bispecific antibodies). Although armed antibodies have shown more potent tumor activity in clinical trials, there have been unacceptably high levels of toxicity. The disadvantage of therapies that rely on delivery of immunotoxins or radionucleotides (direct and indirect arming) has been that these agents are active at all times. There have been problems with damage to non-tumor cells and toxicity issues along with delivery challenges. Many immunotherapies have faced challenges with shed markers and delivery to the intended target. Cancer cells commonly shed antigen targets into the blood stream. Many antibody-based therapies are diluted by interaction with shed antigens. In addition, immune complexes can be formed between the immunotherapeutic and the shed antigen, which can lead to dose-limiting toxicities.

Generation of heat in a range of about 40° C. to about 46° C. (classical hyperthermia) can cause irreversible damage to diseased cells, whereas normal cells are not similarly affected. Diseased tissue may be treated by elevating the temperature of the individual cells contained within to a lethal level (cellular thermotherapy) using a suitable magnetic material confined to the vicinity of the cell and induction heating the material using an alternating magnetic field (AMF).

Hyperthermia may hold promise as a treatment for cancer because it induces instantaneous necrosis (typically called thermo-ablation) and/or a heat-shock response in cells (classical hyperthermia), leading to cell death via a series of biochemical changes within the cell. State-of-the-art systems that employ radio-frequency (RF) hyperthermia, such as annular phased array systems (APAS), attempt to tune E-field energy for regional heating of deep-seated tumors. Such techniques are limited by the heterogeneities of tissue electrical conductivities and that of highly perfused tissues, leading to the unsolved problems of 'hot spot' phenomena in unintended tissues with concomitant under-dosage in the desired areas. These factors make selective heating of specific regions with such E-field dominant systems very difficult.

Another strategy that utilizes RF hyperthermia requires surgical implantation of microwave- or RF-antennae or self-regulating thermal seeds. In addition to its invasiveness, this approach provides only limited (if any) treatment options for metastases because it requires knowledge of the precise location of the tumor, and is thus incapable of targeting undetected individual cancer cells or cell clusters not immediately adjacent to the primary tumor site. Clinical outcomes of these techniques are limited by problems with deposition of physical power to the desired tumor tissues.

Hyperthermia for cancer treatment using colloidal single domain magnetic suspensions (i.e., magnetic fluids) exposed to RF fields has been recognized for several decades. However, a major problem with magnetic fluid hyperthermia has been the inability to selectively deliver a lethal dose of particles to the tumor cells.

SUMMARY OF THE INVENTION

In view of the above, there is a need for a device for a safe and effective hyperthermia based device that involves the selective delivery of magnetic fields to diseased tissue. It is also desirable to have methods for treating diseased tissue, that incorporate selective delivery of magnetic fields to the diseased tissue in a safe and effective manner, with minimal invasion, and short treatment periods.

It is, therefore, an object of the present invention to provide a device capable of delivering an alternating magnetic field of known and controllable amplitude to a specific area of the body.

It is another object of the present invention to provide a device that can treat diseased tissue in a safe and effective manner.

It is another object of the present invention to provide a method that utilizes the devices of the present invention in conjunction with compositions of nanoscale magnetic materials and target-specific ligands to treat diseased tissue via hyperthermia.

It is a further object of the present invention to provide methods for the treatment of diseased tissue in a safe and effective manner, with minimal invasion, and short treatment periods.

The present invention pertains to devices for treating diseased tissue, such as cancer, by interacting with magnetic particles targeted to diseased cells in a patient. Such a device comprises a magnetic generator having a magnetic circuit defining at least part of a magnetic circuit, two poles of the magnetic circuit defining a gap therebetween, a magnetic field passing between two poles, the gap being of sufficient size to receive a portion of the patient containing the disease cells or targeted entities; and a power supply coupled to provide energy to the magnetic generator so that the magnetic field passing between the two poles alternates at a frequency of about 1 kHz or more.

The present invention also pertains to methods for the treatment of diseased tissue with the devices of the present invention. One such method comprises the administration to the patient of a magnetic material composition that comprises at least one magnetic particle attached to a ligand specific to a diseased-cell, and application of an alternating magnetic field to a region of the patient containing the diseased cells so as to inductively heat the magnetic material composition and kill the diseased cells.

The therapeutic device and methods of the present invention provide means for the treatment of diseased tissue in a safe and effective manner, with minimal invasion, and short treatment periods.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
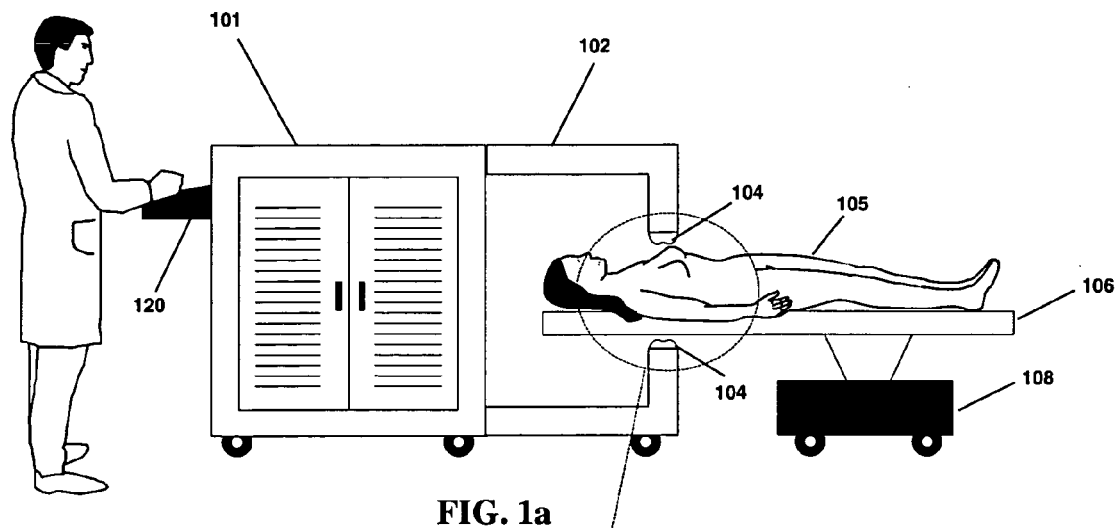
FIG. 1a schematically illustrates a thermotherapy treatment system, according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention pertains to devices for treating diseased tissue, and methods for treating diseased tissue utilizing such devices and magnetic material compositions. The devices and methods of the present invention may be used for the treatment of a variety of indications, including cancer. The methods of therapy using the disclosed device comprise the administration of a therapeutic composition comprising magnetic particles to a patient, and the application, via said device, of an alternating magnetic field to an area of the patient containing the magnetic particle composition to heat the bioprobes sufficiently to kill targeted cells. The present invention, or aspects thereof, may be amenable to use in conjunction with other methods or apparatus.

1. Definitions

The term "bioprobe", as used herein, refers to refers to the composition comprising at least a magnetic particle, a biocompatible coating material, and a target-specific ligand.

The term "core", as used herein, refers to the certain sections of a magnetic circuit that comprise a magnetic material; the purpose of the core is to lower magnetic reluctance.

The term "device", as used herein, refers to a combination of components that comprise the apparatus of the present invention. However, one or more component may be functional as a stand-alone device outside of the purposes of the present invention.

The terms "diseased tissue" or "diseased cell", as used herein, refer to tissue or cells associated with any type of a cancer, diseases of the immune system, pathogen-borne diseases, hormone-related diseases, and undesirable matter, such as toxins, reaction-by-products associated with organ transplants, and other abnormal cell or tissue growth.

The term "hyperthermia", as used herein, refers to an effected increase in physiologic temperature of the diseased tissue such that eventual death of the diseased tissue results. This may comprise, but is not limited to classical hyperthermia, ablation, other necrotic tissue death, or initiation of apoptotic cell death.

The term "ligand", as used herein, refers to a compound which targets biological markers. Examples of ligands include proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, imprinted polymers, and the like.

The term "magnetic circuit", as used herein, refers to a specific route leading from one magnetic pole to the opposite pole in which materials have been placed to reduce magnetic reluctance and to provide a preferred path for the magnetic flux.

It is to be understood that the singular forms of "a", "an", and "the", as used herein and in the appended claims, include plural reference unless the context clearly dictates otherwise.

2. The Targeted Delivery Device

The targeted delivery device of the present invention, an embodiment of which is illustrated in FIG. 1a, comprises an alternating magnetic field (AMF) generator located within a cabinet 101 designed to produce an alternating magnetic field (AMF) that may be guided to a specific location within a patient 105 by a magnetic circuit 102. The therapeutic methods of the present invention may be performed following a diagnosis or evaluation of cancer or a pre-cancerous condition or other disease in one or more areas of the patient. The manner of making the diagnosis does not form part of the invention and may be performed using any standard method. The patient lies upon an X-Y horizontal and vertical axis positioning bed 106. The bed 106 is both horizontally and vertically positionable via a bed controller 108. The AMF generator produces an AMF in the magnetic circuit 102 that exits the magnetic circuit at one pole face 104, passing through the air gap and the desired treatment area of the patient, and reenters the circuit through the opposing pole face 104, thus completing the circuit. An operator or medical technician is able to both control and monitor the AMF characteristics and bed positioning via the control panel 120. The AMF is generated by passing electrical current through one or more coils that surround the magnetic circuit. These coils may be part of a resonant circuit. Alternatively, these coils may be driven by an amplifier or by pairs of diode isolated pulse forming networks, switched by either solid state or vacuum tube devices.

In one embodiment of the present invention, the disclosed device is utilized for the treatment of a patient with cancer, as illustrated in FIG. 1a. An area 103, containing diseased tissue, of a patient 105 is localized in the region between magnetic poles 104 via a positionable bed 106. An AMF may be applied to the treatment area 103 of the patient 105, as illustrated by the magnetic lines of flux 112. The magnetic field, manifested by the magnetic lines of flux 112, interacts with both healthy and diseased tissue in the localized area. The bioprobes 110, containing at least one appropriate ligand selective to the particular type of breast cancer, are bound to cancer cells 114. In this embodiment, the bioprobes 110 are selective to breast cancer. The bioprobes 110 become excited by the interacting applied AMF and are inductively heated to a temperature sufficient to kill diseased or cancerous cells. Heat generated in the excited the bioprobes 110 passes to the cancer cells 114, thereby causing the cancer cells 114 to die.

It will be appreciated that other types of cancers, such as lung, prostate and the like, and other types of indications, such as diseases of the immune system, pathogen-borne diseases, non-cancerous diseased cells or tissue, and undesirable matter, such as toxins, reaction-by-products associated with organ transplants, hormone-related diseases, may be treated using the device of the present invention. Further, the poles 104 may be formed from pieces the gap of which is adjustable, so as to permit other parts of the body of patient 105 to be treated. It is advantageous to set the gap between the poles 104 to be sufficiently large to permit the part of the body containing the cancer to enter the gap, but not be so large as to reduce the magnetic field strength.

Figure 2A:
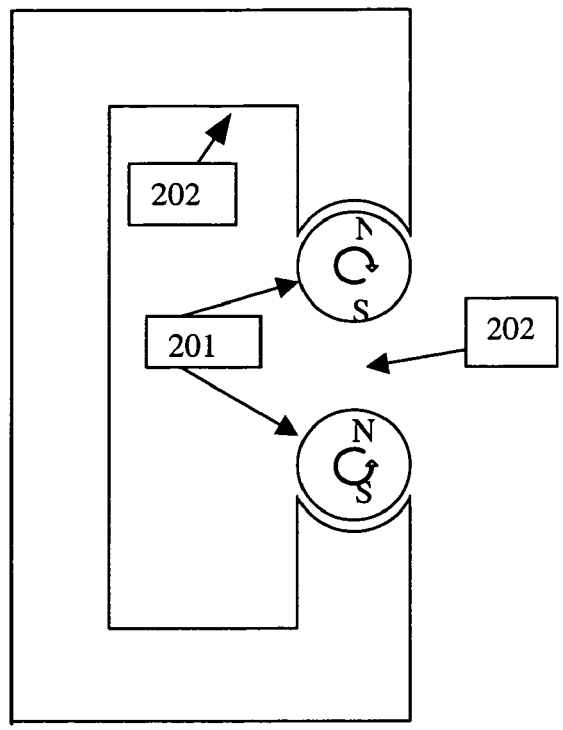
FIG. 2a schematically illustrates an alternative source of AMF, according to an embodiment of the present invention.

In one embodiment, an alternate means of producing AMF is utilized, as illustrated in FIG. 2a. Here, the device comprises two cylindrical magnets 201 that are charged across their respective diameters, and a magnetic circuit 202 to guide the magnetic flux. The cylindrical magnets 201 are aligned as shown, and synchronously rotated, yielding an AMF in a gap 203.

Figure 2B:
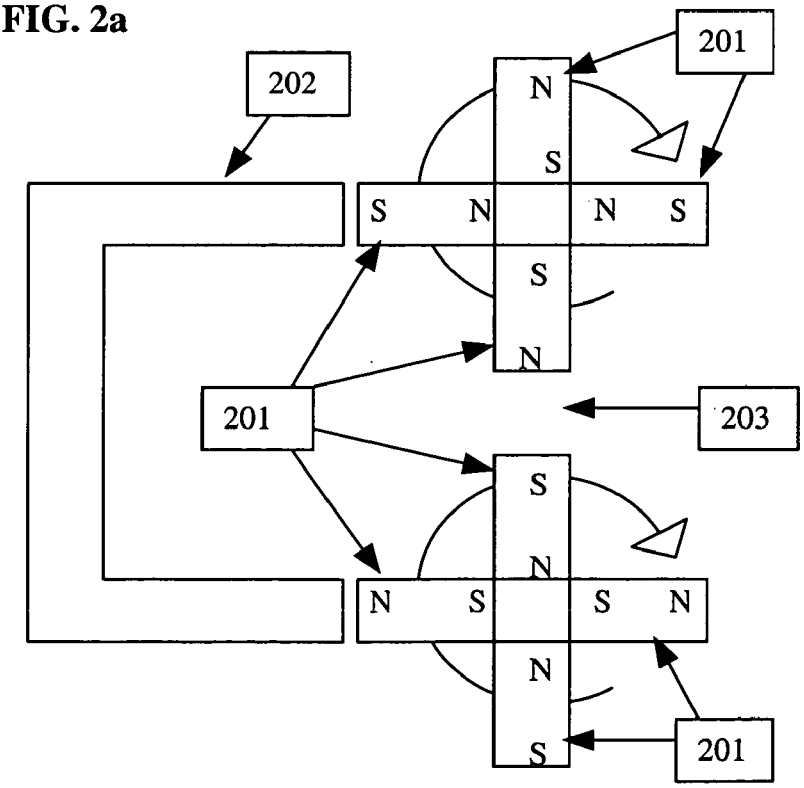
FIG. 2b schematically illustrates an alternative source of AMF, according to an embodiment of the present invention.

In another embodiment, which is a variation of the device illustrated in FIG. 2a, the synchronously rotating bodies contain more than one pair of magnets 201, as illustrated in FIG. 2b. While the device illustrated in FIG. 2a creates one cycle of AMF for each rotation, the device illustrated in FIG. 2b doubles the frequency for a given rotational velocity. Additional pairs of magnets 201 may be added to the rotating bodies until doing so is no longer practical due to the leakage flux between angularly adjacent magnets 201 which will significantly limit the amount of magnetic flux traveling through the gap 203.

Figure 3:
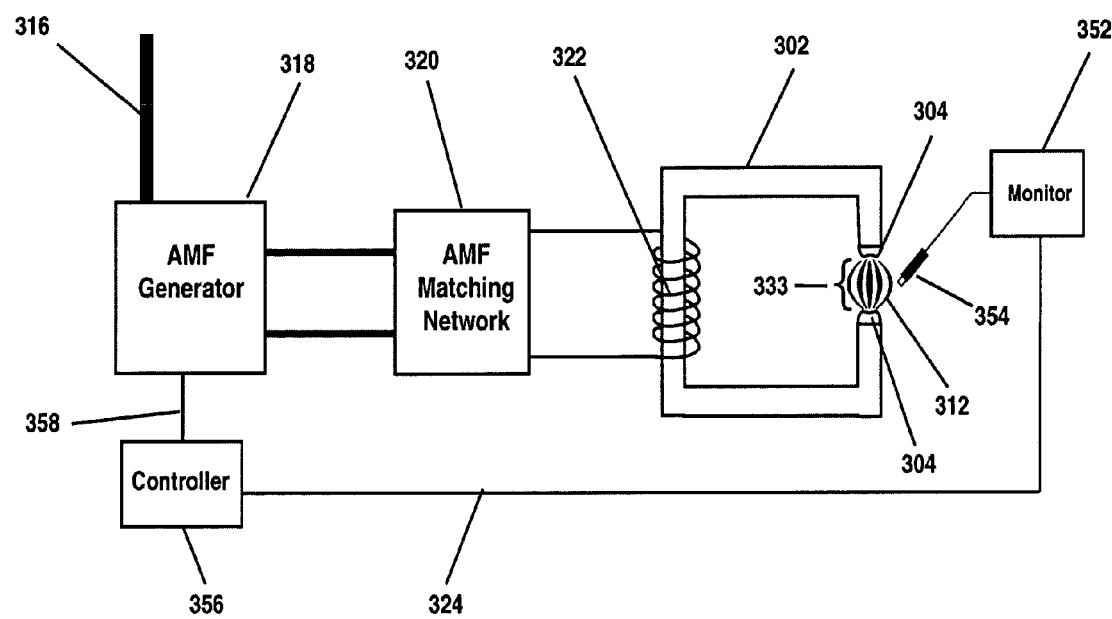
FIG. 3 schematically illustrates a circuit for producing a thermotherapeutic alternating magnetic field, according to an embodiment of the present invention.

In another embodiment of the present invention, another apparatus is used for producing an AMF, as illustrated in FIG. 3. An AMF generator 318 is supplied with alternating current (AC) power via a conduit 316. A circulating fluid supply is also provided in the conduit 316. The AMF generator 318 may become hot, and it may be cooled with the circulating fluid supply while in operation. The fluid may be water; however a fluid such as silicone oil or other inorganic or organic (carbon based) fluids with suitable thermal and electric properties may be preferable. The energy produced by the generator 318 is directed through an AMF matching network 320 where the impedance of the generator is matched to the impedance of a coil 322. The impedance of the AMF matching network 320 may be adjustable to minimize the energy reflected back to the generator 318. In another embodiment, the generator frequency may be automatically adjusted to minimize the reflected energy. The modified energy may be directed to the magnetic circuit 302. An AMF is induced in the magnetic circuit 302 as a result of the current passing through the coil 322. Magnetic lines of flux 312 are produced in the gap 333 between the poles 304 in the magnetic circuit 302. A feedback loop 324 may be provided for monitoring the magnetic field profile in the gap 333 between the poles 304. A suitable probe 354 provides data to a monitor 352, which relays information to a controller 356 via an appropriate data bus 324. Information from the controller 356 is relayed to the generator 318 via an appropriate data bus 358. Monitoring the magnetic field profile may be useful in detecting the presence of magnetic particles, or undesired conductive or magnetic materials such as implants or foreign objects. Monitoring the inductance of tissue and monitoring the temperature of tissue located in the gap 333 is useful for insuring patient safety.

Figure 4A:
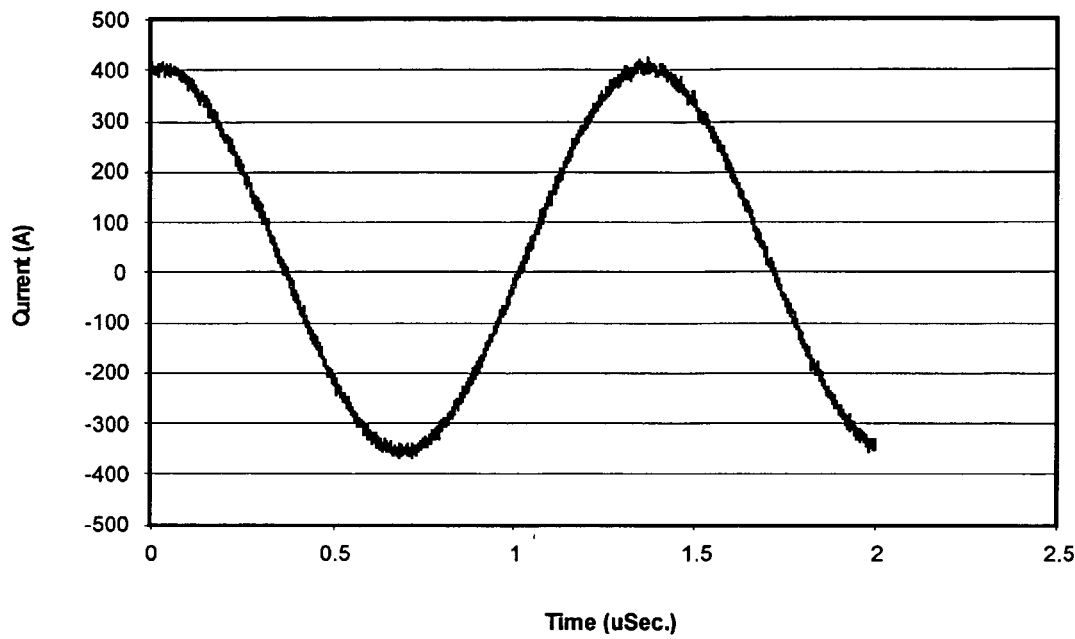
FIG. 4a graphically illustrates a thermotherapeutic sinusoidal current waveform, according to an embodiment of the present invention.
Figure 4B:
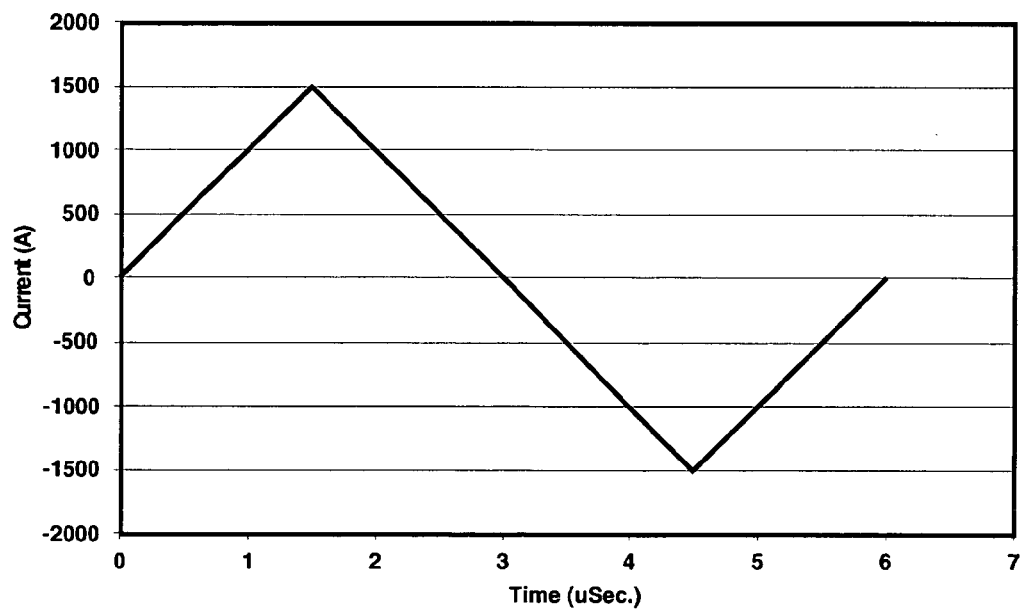
FIG. 4b graphically illustrates a thermotherapeutic triangular current waveform, according to an embodiment of the present invention.

Measuring alternating magnetic fields directly is extremely difficult. Because the AMF is proportional to the current in the coil 322, characteristics of the AMF may be defined in terms of the coil current, which can readily be measured with available test equipment. For example, the coil current may be viewed and measured with a calibrated Rogowski coil and any oscilloscope of suitable bandwidth. The fundamental waveform may be observed as the direct measure of the magnitude and direction of the coil current. Many different types of fundamental waveforms may be used for the AMF. For example, FIG. 4a illustrates a sinusoidal current waveform, and FIG. 4b illustrates a triangular current waveform. The shape of the fundamental waveform may also be square, sawtooth, or trapezoidal.

Most practical generators produce an approximation of these waveforms with some amount of distortion. In most applications, this waveform may be nearly symmetrical around zero, as illustrated in FIG. 4a and FIG. 4b. However, there may be a static (or DC) current superimposed on the waveform (DC offset). A DC offset may be useful in attracting the bioprobes to the treatment area. A DC offset of equal or greater amplitude than the AC component could be especially useful in attracting bioprobes to the treatment area and may be employed prior to the treatment to enhance efficacy. FIG. 4a and FIG. 4b show at least one cycle of two different fundamental waveforms with zero or near zero DC offsets. The fundamental period may be defined as the time it takes to complete one cycle. The fundamental frequency may be defined as the reciprocal of the fundamental period. The fundamental frequency may be between 1 kHz and 1 GHz, preferably between 50 kHz and 15 MHz, and more preferably between 100 kHz and 500 kHz. The fundamental frequency may be intentionally modulated (as in many high-resolution RADAR designs), and may often vary slightly as a result of imperfections in the RF generator design.

Figure 5A:
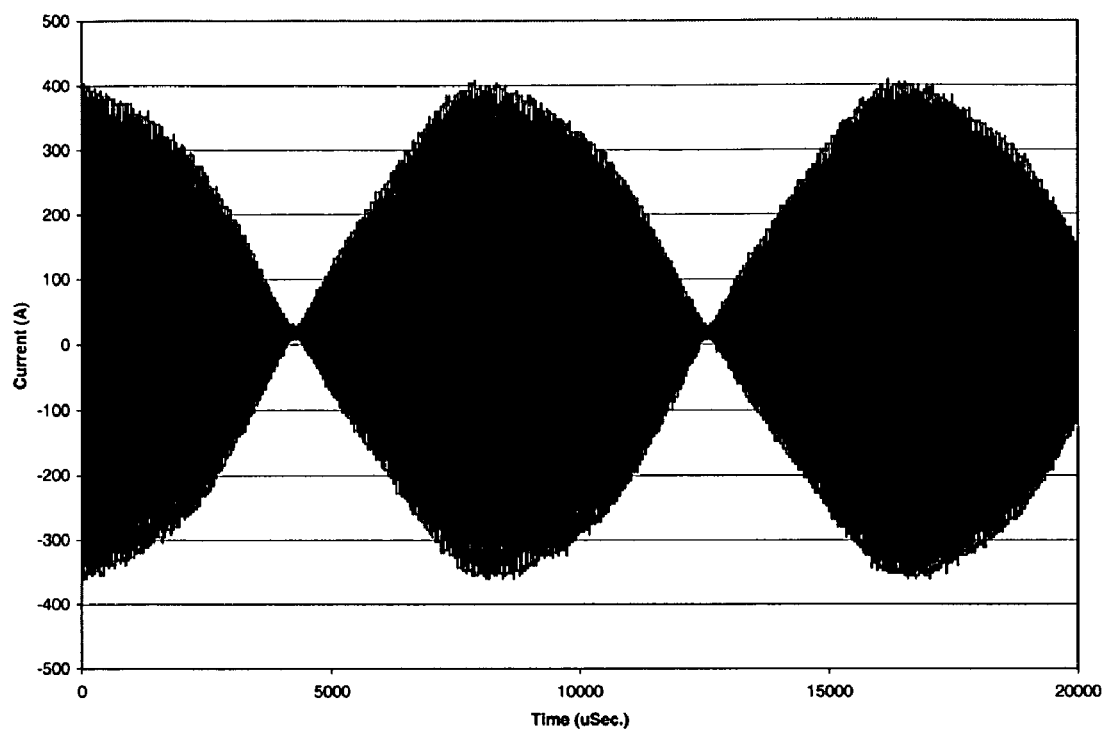
FIG. 5a graphically illustrates a thermotherapeutic sinusoidal waveform modulation, according to an embodiment of the present invention.
Figure 5B:
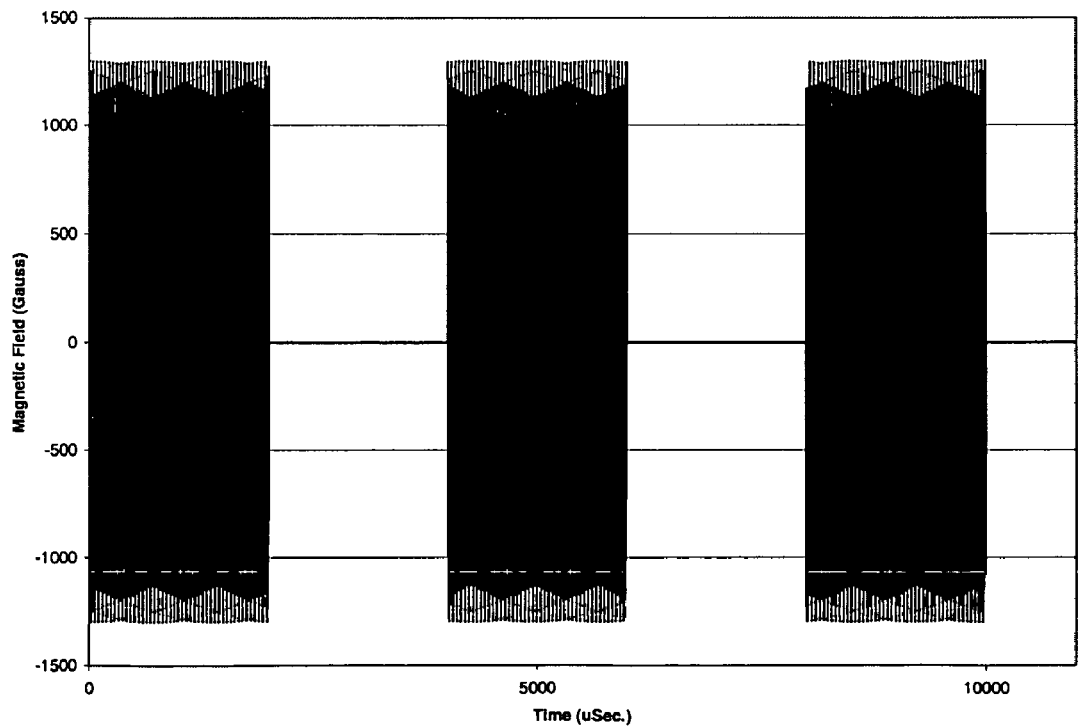
FIG. 5b graphically illustrates a thermotherapeutic pulsed waveform modulation, according to an embodiment of the present invention.

The amplitude of the waveform may also be modulated. FIG. 5a illustrates an embodiment in which a sinusoidal current modulation envelope is used, and FIG. 5b illustrates an embodiment that utilizes a square modulation envelope. The shape of the amplitude modulation envelope may typically be sinusoidal, square, triangular, trapezoidal or sawtooth, and may be any variation or combination thereof, or may be some other shape.

The AMF produced by the generator may also be pulsed. Pulse width is traditionally defined as the time between the −3 dBc points of the output of a square law crystal detector. Because this measurement technique is cumbersome in this application, we use an alternate definition of pulse width. For the purpose of this invention, pulse width may be defined as the time interval between the 50% amplitude point of the pulse envelope leading edge and the 50% amplitude point of the pulse envelope trailing edge. The pulse width may also be modulated.

The pulse repetition frequency (PRF) is defined as the number of times per second that the amplitude modulation envelope is repeated. The PRF is typically in the range between 0.0017 Hz and 1000 MHz. The PRF may also be modulated. The duty cycle may be defined as the product of the pulse width and the PRF, and thus is dimensionless. In order to be defined as pulsed, the duty of the generator 318 must be less than unity (or 100%).

The AMF may be constrained to prevent heating healthy tissue to lethal temperatures (typically $\geq 43°$ C.). This may be accomplished in a variety of ways.

The peak amplitude of the AMF may be adjusted.

The PRF may be adjusted.

The pulse width may be adjusted.

The fundamental frequency may be adjusted.

These four characteristics may be adjusted to maximize heating rate of the bioprobes and, simultaneously, to minimize the heating rate of the healthy tissue located within the treatment volume. These conditions may vary depending upon tissue types to be treated, thus the operator may determine efficacious operation levels. In one embodiment, one or more of these characteristics are adjusted during treatment based upon one or more continuously monitored physical characteristics of tissue in the treatment volume by the probe 354, such as temperature or impedance. This information is then supplied as input to the generator 318, via the monitor 352, the data bus 324, the controller 356, and the data bus 358 to control output. The generator output may be adjusted so that the peak AMF strength is in the range between about 10 Oersteds (Oe) and about 10,000 (Oe). Preferably, the peak AMF strength is in the range between about 20 Oe and about 3000 Oe, and more preferably, between about 100 Oe and about 2000 Oe.

In another embodiment of the present invention, the differential heating of the bioprobes, as compared to that of the healthy tissue, is maximized. The bioprobes 210 heat in response to each cycle of the AMF. Assuming the fundamental frequency, the PRF, and the pulse width remain constant, the heat output of the bioprobe 210 continues to increase as peak amplitude of the AMF increases until the magnetic material of the bioprobe reaches saturation. Beyond this point, additional increases in AMF amplitude yield almost no additional heating. However, at AMF amplitudes below saturation, it can be said that bioprobe heating is a function of AMF amplitude. Unlike bioprobes, healthy tissue heating is a result of eddy current flow and a function of the rate of change of the AMF. In particular, the eddy current and resultant tissue heating are described by the following expressions:

$$I_{eddy} \propto dB/dT \tag{1}$$

$$\text{Tissue Heating} \propto I_{eddy}^2 \tag{2}$$

From the relationships (1) and (2), it is evident that reducing the rate of change of the AMF yields a significant reduction in tissue heating. In one embodiment of the present invention, this relationship is exploited by using a symmetrical triangular wave as the fundamental waveform, as shown in FIG. 4b. By avoiding the high rates of change as a sinusoid crosses the X-axis (FIG. 4a), and substituting the constant but lower rate of change associated with a triangular waveform (FIG. 4b), tissue heating is reduced with little or no sacrifice in bioprobe heating. A triangular waveform, as shown in FIG. 4b, is achieved by using an appropriate generator, such as a linear amplifier-based generator. Some distortion of the triangle is inevitable, but tangible reductions in tissue heating result from even small reductions in dB/dT.

Figure 8:
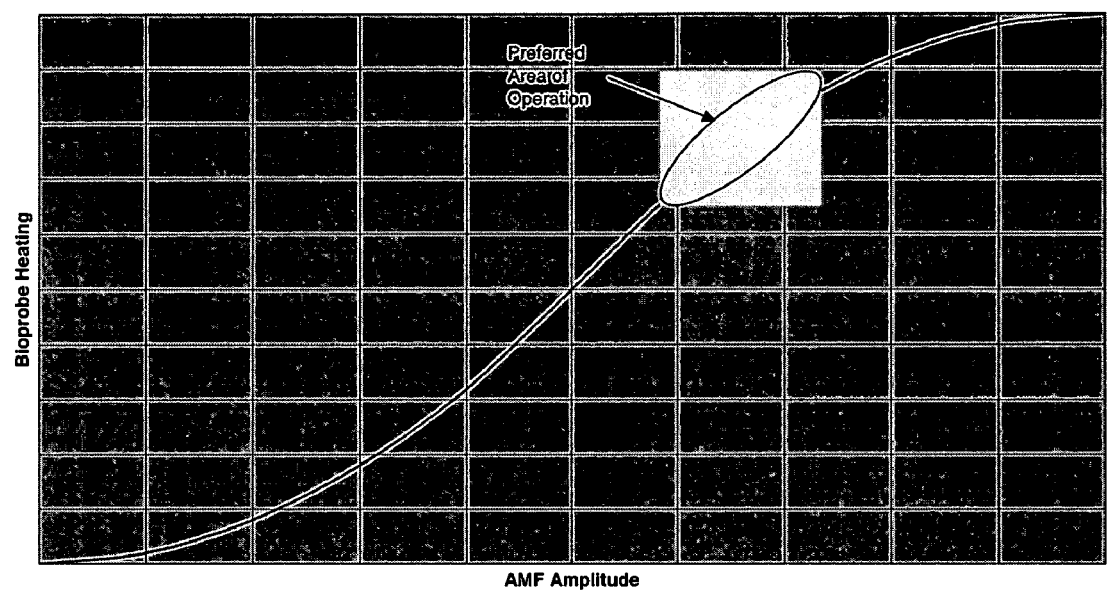
FIG. 8 graphically illustrates the relationship between bioprobe heating and AMF amplitude, according to an embodiment of the present invention.

The heating of both the tissue and the bioprobes increase with increased AMF amplitude. At low AMF amplitudes, small increases yield significant increases in magnetic heating. As the bioprobes approach saturation however, their relationship with the AMF amplitude becomes one of diminishing return. This relationship is unique to the particular magnetic material, as are the values that constitute "low" or "saturating" AMF amplitudes. Bioprobe heating is at first related to the AMF amplitude by an exponent >1, which gradually diminishes to an exponent <1 as saturation is approached. FIG. 8 illustrates the relationship between bioprobe heating and AMF amplitude for a typical magnetic material. At typical pulse widths and duty cycles, eddy current heating is directly related to duty cycle. The capability to pulse the generator output, as illustrated in FIG. 5a and FIG. 5b, allows the benefits of operating at higher AMF amplitudes while maintaining a constant reduced tissue heating by reducing the duty cycle.

Figure 1B:
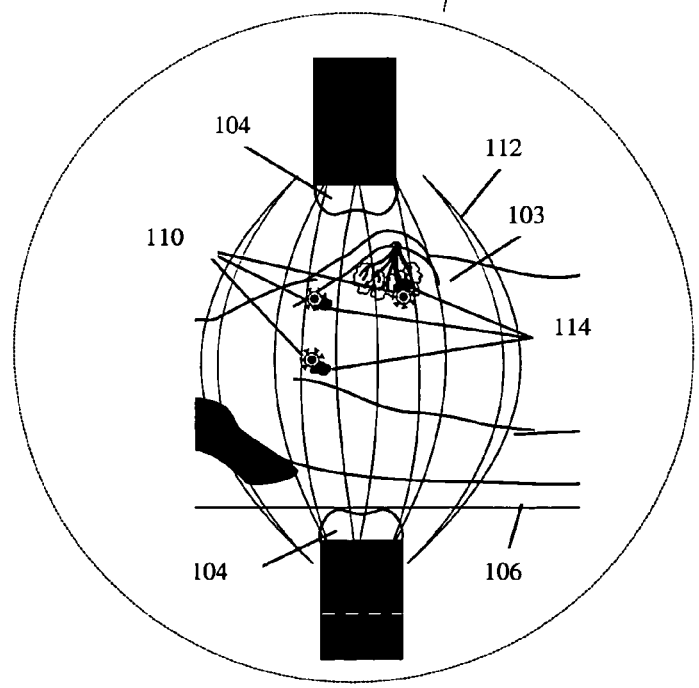
FIG. 1b schematically illustrates a thermotherapy treatment, according to an embodiment of the present invention.

It is desirable to apply the AMF to the treatment area 103 of the patient 105. Generating high peak amplitude AMF over a large area requires a very large AMF generator and exposes large amounts of healthy tissue to unnecessary eddy current heating. Without some means of directing the field to where it is useful, disease in the chest or trunk could only be practically treated by placing the patient within a large solenoid coil. This would expose most of the major organs to eddy current heating, which must then be monitored and the AMF adjusted so as not to overheat any part of a variety of tissue types. Each of these tissue types has a different rate of eddy current heating. The peak AMF strength would need to be reduced to protect those tissue types that experience the most extreme eddy current heating. If the varieties of exposed tissue are minimized, it is likely that the AMF strength can be increased, and thereby reducing the treatment time and increasing the efficacy. One method for confining the high peak amplitude AMF to treatment area 103 involves defining the lowest reluctance path of magnetic flux with high permeability magnetic material. This path is referred to as a magnetic circuit (102 in FIGS. 1 and 302 in FIG. 3), and it is also commonly referred to as a magnetic core in the induction heating industry, and as a return path in the design of DC magnetic circuits. The magnetic circuit may be provided so that all or most of the magnetic flux produced by the coil 322 is directed to the treatment area 103. One benefit of the magnetic circuit 302 is that the necessary amount of flux may be reduced as the amount of flux extending beyond the treatment area 103 is minimized. Reducing the required flux reduces the required size and power of the AMF generator, and minimizes exposure of tissue outside the treatment area 103 to high peak amplitude AMF. In addition, a reduced area of AMF exposure avoids the unintentional heating of surgical or dental implants and reduces the likelihood that they will need to be removed prior to treatment, thereby avoiding invasive medical procedures. Concentrating the field permits the treatment of large volumes within the chest or trunk with a portable size device.

The material used for fabricating the magnetic circuit 302 may be appropriate to the peak amplitude and frequency of the AMF. The material may be, but is not limited to, iron, powdered iron, assorted magnetic alloys in solid or laminated configurations, magnetic fluids and paste, magnetic material suspended in a polymer matrix, such as Fluxtrol® (available from Fluxtrol Inc. Auburn Hills Mich.), and ferrites. The pole faces 104 and 304 may be shaped and sized to further concentrate the flux produced in the treatment area. The pole faces 304 may be detachable. Different pole pieces having different sizes and shapes may be used as pole faces 304 so that the treatment area and volume may be adjusted. When passing from one material to another, the lines of magnetic flux 312 travel in a direction normal to the plane of the interface plane. Thus, the pole face 304 may be shaped to influence the flux path through gap 333. As the gap 333 between pole faces 304 increases relative to the pole diameters, this technique becomes less useful. The pole faces 304 may be detachable and may be chosen to extend the magnetic circuit 302 as much as possible, to minimize the gap 333 while leaving sufficient space to receive that portion of the patient being treated.

Figure 6A:
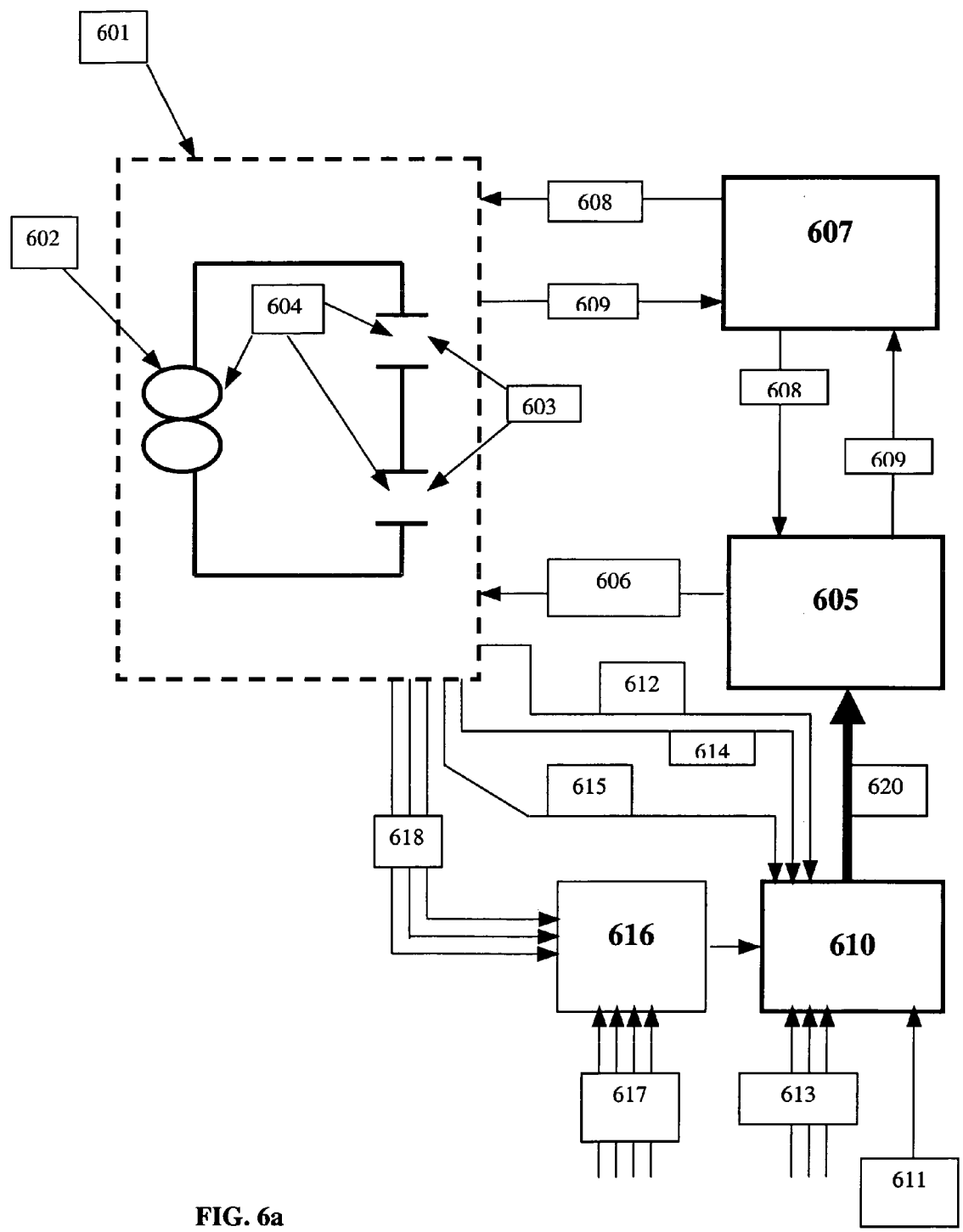
FIG. 6a schematically illustrates the relationship between the device components, according to an embodiment of the present invention.
Figure 6B:
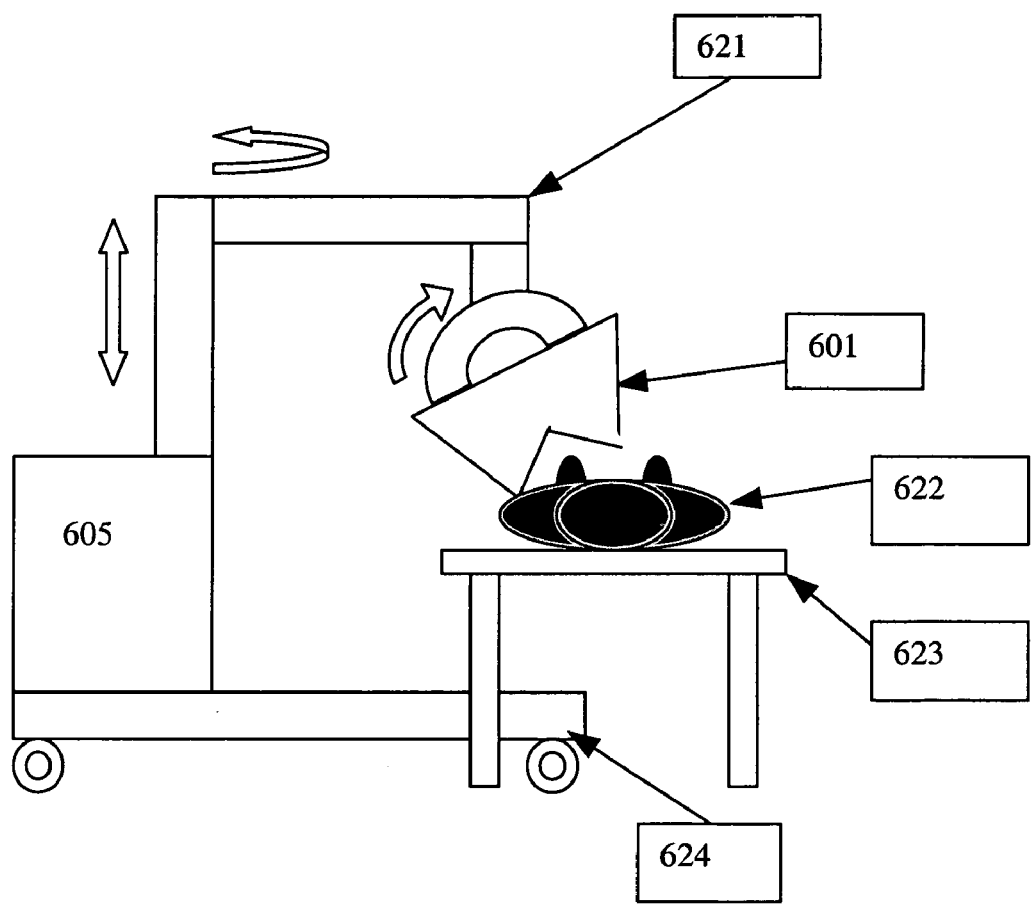
FIG. 6b schematically illustrates a thermotherapy treatment system, according to an embodiment of the present invention.

An embodiment of the invention for use in treating diseases that are located closer to the surface of a patient's body is illustrated in FIG. 6a and FIG. 6b. The treatment head 601 is comprised of AMF coils 602, magnetic circuit (not shown) and matching capacitors 603, which together constitute a resonant network 604. An RF power supply 605 excites the resonant network 604 with a pulsed DC signal 606. A coolant chiller 607 is provided to cool the components of the treatment head 601 as well as the RF power supply 605. Coolant supply lines 608 and coolant return lines 609 deliver and return coolant in parallel closed loops. A treatment controller 610 controls the output characteristics of the RF power supply 605 via a master control bus 620 in response to operator input 611 (assigning duty, pulse width, treatment time, etc.), coolant flow sensors 612 (to prevent component overheating), AMF amplitude sensors 613 (to insure prescribed AMF amplitude and to sense conductive or magnetic objects in or near the treatment area), circuit impedance sensors 614 (to sense conductive or magnetic objects in or near the treatment area), frequency sensors 615 (also to sense conductive or magnetic objects in or near the treatment area) and to a temperature probe controller 616. The temperature probe controller 616 monitors multiple channels of patient temperature sensors 617, to insure patient safety, and equipment temperature sensors 618, to insure safe operating temperatures, for the various system components. The temperature probe controller 616 converts the data to a digital format and sends it to the treatment controller 610. The treatment controller 610 software can then respond to unsafe or unplanned temperatures in the patient or in the equipment by altering or curtailing the treatment protocol.

A support arm 621 (shown only in FIG. 6a) holds the treatment head 601 in position to treat the appropriate area of a patient 622. To assist in positioning, the support arm 621 has angular and height adjustments as shown. The treatment head 601 also has an angular adjustment as shown. A treatment table 623 (shown only in FIG. 6a) is constructed of non-conductive, non-magnetic materials so that it will not interact with, or be heated by, the AMF. The support arm 621 and power supply 605 are mounted on a moveable cart 624 (shown only in FIG. 6a) to further aid in positioning.

Figure 6C:
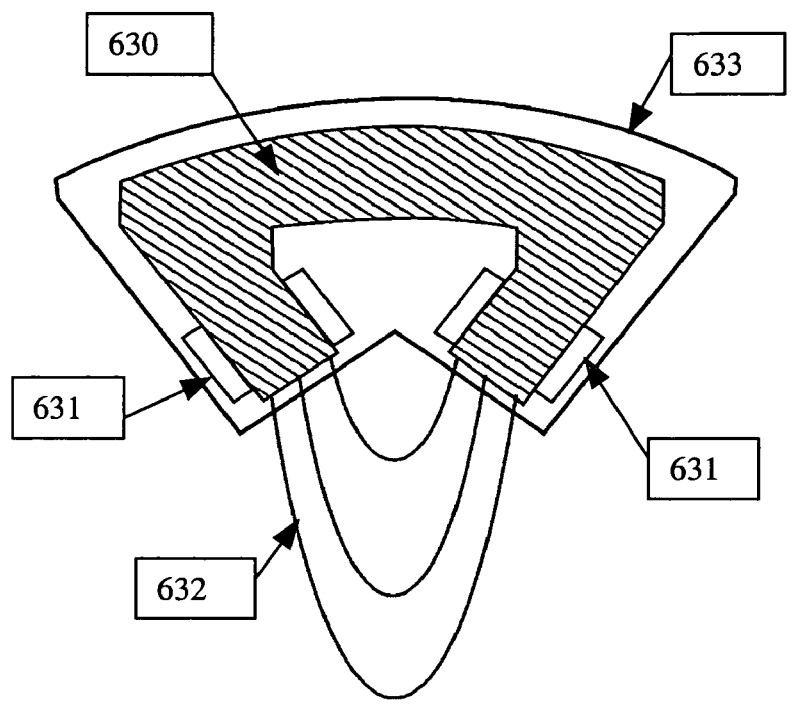
FIG. 6c schematically illustrates a cross-sectional view of a treatment head, according to an embodiment of the present invention.

A cross sectional view of a treatment head 601 that may be used in the system described in FIG. 6a and FIG. 6b is illustrated in FIG. 6c. A magnetic circuit 630 is surrounded in two locations by coils 631 and terminates at pole faces 634. When current flows through the coils 631, a magnetic field 632 is generated. The treatment head 601 is housed within a structural insulating material, 633 to protect the patient 622.

Figure 6D:
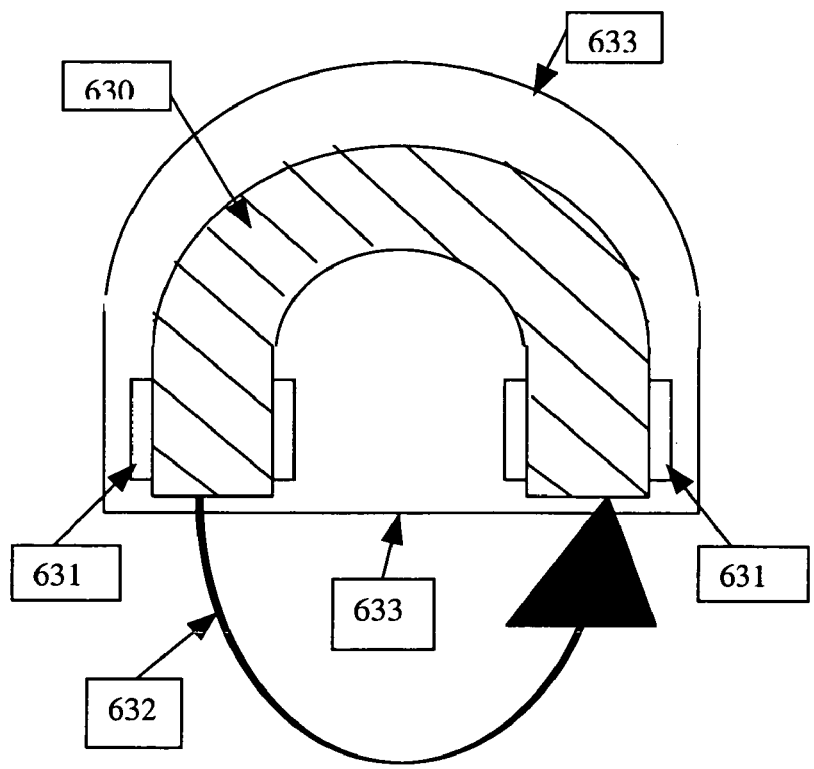
FIG. 6d schematically illustrates a cross-sectional view of a treatment head, according to an embodiment of the present invention.

Alternative configurations of the treatment head 601 may also be useful in the present invention, an example of which is illustrated in FIG. 6d. The magnetic circuit 630 is surrounded in two locations by the coils 631 and terminates at the pole faces 634. When current flows through the coils 631, a magnetic field 632 is generated. The treatment head 601 is housed within a structurally insulating material 633 to protect the patient 622.

In one embodiment of the present invention, the coils (322 in FIG. 3, 631 in FIG. 6c) are located anywhere on the magnetic circuit (302 in FIG. 3, 630 in FIG. 6c). They may be located close to the pole faces as in FIG. 6c, to maximize the magnetic field amplitude. Alternatively, they may be located away from the pole faces as in FIG. 3, to minimize the engineering challenges of protecting the patient from high operating temperatures and high voltage.

In one embodiment of the present invention, the surface area of the coils is increased to enhance conductivity due to skin effect as well as to aid in the removal of heat.

In one embodiment, helper coils are utilized to confine or alter the distribution of magnetic flux. These helper coils may be wired in series or in parallel with the main coils, and their phase is adjusted to best enhance the therapy. They can be positioned to maximize magnetic flux in the treatment area or positioned to divert magnetic flux from a specific area. The helper coils may also be powered by a separate power supply as long as they are phase locked to the main coils.

In one embodiment, the magnetic circuit is omitted and an air return path used. Multi-turn coils of decreasing diameter, oriented such that the smallest diameter turns are closest to the patient, are used to increase the peak AMF amplitude in the gap. Alternatively, single-turn conical shaped coils may be used, with their narrow end closest to the patient, to accomplish the same. Either of these coil types may also be used in a configuration comprising a magnetic circuit or a partial magnetic circuit.

Figure 7:
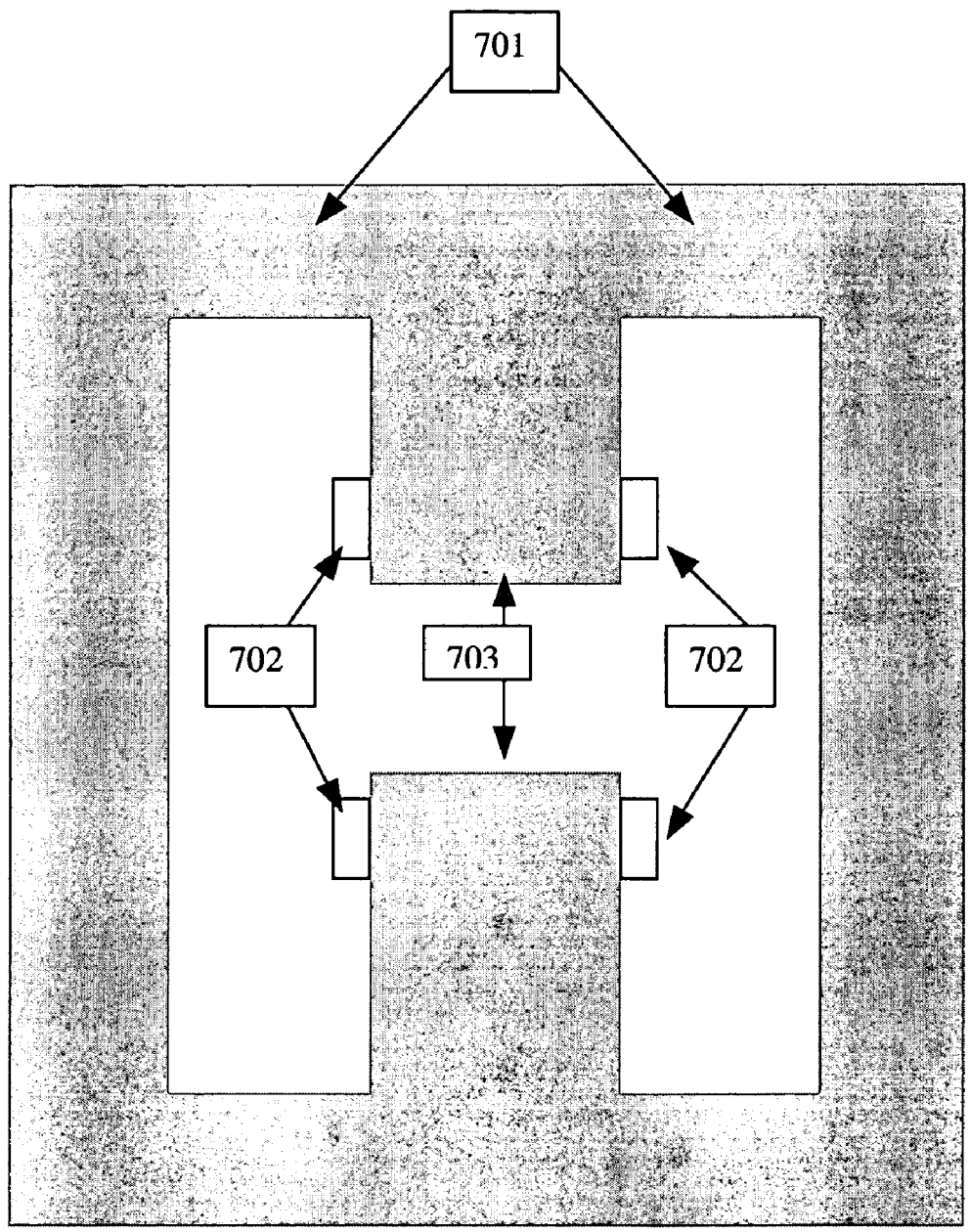
FIG. 7 schematically illustrates a cross-sectional view of a magnetic circuit, according to an embodiment of the present invention.

In one embodiment of the present invention, multiple magnetic circuits 701 may be used in parallel, as illustrated in FIG. 7. Because coils 702 are typically hollow and filled with circulating coolant, poles 703 will also be cooled due to their proximity to the coils 702. As the distance from the coils 702 increases, the heat path becomes longer and cooling efficiency is reduced. By providing two magnetic circuits 701, the magnetic flux in each is halved and the heat generated in each becomes more manageable.

It is preferable that the AMF is used efficiently to heat bioprobes. FIG. 8 illustrates the relationship between bioprobe heating and AMF amplitude. For typical magnetic materials, the relationship is exponential with the exponent being <1 at low AMF amplitude, gradually increasing to >1 as AMF increases and returning to <1 as saturation is reached. Because of this relationship, the most efficient use of AMF to heat the bioprobes occurs at amplitudes in the area marked "Preferred Area of Operation". For many materials, this AMF amplitude would cause unacceptable rates of eddy current heating of tissue. To mitigate this undesired collateral heating, the AMF is preferably pulsed and the duty adjusted to safe levels for the treatment duration.

In one embodiment of the present invention, numerical simulations are used to plan the treatment procedure. The method of planning the treatment procedure involves simulation of the magnetic flux in a patient's body, utilizing the pole geometry and electrical parameters of the coils. From an anatomical conductivity tissue model, the specific absorption rate for magnetic energy and eddy current heating are simulated. The optimal treatment parameters are then determined by iteratively adjusting the electromagnetic parameters (e.g., frequency, coil current, pulse shape, pulse repetition envelope, pulse repetition frequency, duration, duty cycle, and magnet position) in the magnetic flux simulation to yield an optimal treatment plan. In this manner, the energy necessary for heating the particles in the diseased tissue is maximized while the eddy current heating of the healthy tissue is minimized.

In one embodiment of the present invention, thermoplastic masking is used to fix the location of a patient's body relative to the AMF, and to aid in targeting the desired treatment area, as used in the same manner as in imaging applications and in some radio, laser and ultrasonic therapies and procedures.

EXAMPLES

Having generally described the invention, a more complete understanding thereof may be obtained by reference to the following examples that are provided for purposes of illustration only and do not limit the invention.

Example 1

Pulsed Operation for Increased Bioprobe Heat Output

In general, a fundamental frequency of several MHz is effective for inductive heating. At such frequencies, however, tissue heating may be problematic. Because eddy current heating of the tissue is approximately proportional to the square of the frequency and hysteretic heating of the particles is approximately proportional to frequency to the first power, lower frequency tends to favor hysteretic heating. More precisely, reducing the frequency yields a greater reduction in tissue heating than in bioprobe heating for a specific AMF amplitude.

Eddy current heating of tissue is also proportional to the square of the AMF amplitude. Hysteretic heating of the bioprobes has a more complex relationship with AMF amplitude. A typical relationship between AMF amplitude and hysteretic heat output is described in FIG. 8. Tissue heating places limitations on the practical amplitude of the magnetic field. A preferred range may be from about 100 Oe to about 200 Oe, using a constant waveform generator. Difficulties may arise in achieving desired particle heating with many materials when the field falls in this range. The field conditions may also be inadequate because the number of bioprobes attaching to the targeted cells may often be unknown and/or limited by the specifics of cellular biology. The limitation may be overcome by using a pulsed generator and setting the field conditions, field amplitude and pulse characteristics, to levels that heats the bioprobes sufficiently to kill targeted cells without excessive peripheral tissue heating. Thus, under pulsed conditions, peak magnetic fields of up to a few thousand Oersteds (Oe) may be used.

Example 2

Efficacy of Bioprobes: In Vitro Trials with MCF-7 Breast Cancer Cells

The bioprobes used in this example included 50-nm, $Fe_3O_4$ particles surrounded by a dextran shell, to which the monoclonal antibody (mAB) for Her-2 was covalently linked. The particles were suspended in cellular growth media including Modified Eagle's Medium (MEM) containing 10% fetal calf serum, insulin (10 µg/ml), fungizone, glutamine, penicillin, streptomycin, sodium pyruvate and non-essential amino acids, which was then added to cultures of MCF-7 cells. The MCF-7 cells represent an estrogen receptor-positive human breast carcinoma, and were grown on tissue culture inserts with a 10 mm diameter possessing porous frits with pore sizes of 0.02 or 0.2 µm.

The alternating magnetic field source was an industrial 3.5 kW variable duty radio-frequency generator with a frequency of 740 kHz and time-averaged field amplitude of 500 Oe (peak field amplitude, 1300 Oe). The generator produced pulses with a length of 4.174 ms, at a pulse repetition rate of 121 Hz, to give a duty cycle of 50.6%. The generator provided power to a 14-mm (inner diameter), 5-turn copper solenoid coil into which sample containers were inserted. The average temperature of the media in all samples monitored in situ using silicon dioxide temperature probes resistant to electromagnetic (EM) fields (obtained from FISO Technologies Inc., Ste-Foy, Quebec, Canada).

A series of water bath tests was conducted to determine the hyperthermia tolerance of the cell cultures. The purpose of these tests was to obtain "positive control" data on the effects of hyperthermia on the cancer cell cultures and to aid in the interpretation of experiments using the bioprobe system. Exposing cellular culture media to an alternating magnetic field, without the presence of the bioprobes, may cause some tissue heating. Such magnetic induction heating is determined by the frequency and field strength of the magnetic field. Thus, to avoid overheating the media with the applied magnetic field, water bath tests were conducted to provide threshold limits of magnetic induction heating of the media containing cells not receiving the treatment. Table 1 lists results of cell death fraction as a function of exposed temperature and exposure time. The MCF-7 cell line is shown to be unaffected by heat exposure to 42° C. for 30 minutes. Thus, for all in vitro experiments, the magnetic field strengths were fixed at levels where the average temperature of the cellular growth media (containing no cells or magnetic fluid) remained at or below 42° C.

TABLE 1

Result of water bath tests with MCF-7 cells

| Temperature (° C.) | Time Of Exposure (Min.) | % Dead Cells |
| --- | --- | --- |
| 37* | N/A | 4 |
| 42 | 30 | 4 |
| 43 | 15 | 5 |
| 46 | 5 | 92 |

*Represents a control cell culture sample not placed into water bath.

Cells intended for treatment were combined with bioprobes containing the Her-2 antibody and incubated for 8 minutes at 20° C., followed by three rinses with growth media, to remove unattached bioprobes. The cell cultures were analyzed before and 6 hours after the 20-minute treatments with the alternating magnetic field (AMF). The fraction of dead cells for the targeted sample (T1) and control samples (C1-C3) are presented in Table 2. In the targeted sample, 91%±5% (n=7) of the MCF-7 cells were killed. Of the cells killed, about 70% cells were be lysed by the treatment, as measured by spectrophotometric analysis of cytoplasmic lactate dehydrogenase (LDH), an enzyme produced by living cells. The remaining approximately 20% underwent apoptosis, as measured using a commercial fluorescent apoptosis-staining assay. The kill rates for the targeted cells are significantly higher than baseline death and apoptotic rates of 4%±1% in all controls (Table 2). Control groups include: 1) cells receiving no exposure to either the AMF or bioprobes (Sample C1); 2) cells exposed to the bioprobes alone (Sample C2); and 3) cells exposed to the AMF alone (Sample C3). Similar baseline deaths of all controls confirm that neither the AMF alone, nor only the presence of the bioprobes, is toxic to the cells. Higher than normal cell death occurs only when the AMF is applied after the bioprobes have attached to a cell.

TABLE 2

In vitro results with MCF-7 cells

| Sample | Treatment | % dead cells (n = 7) |
| --- | --- | --- |
| C1 | NO BIOPROBES, NO AMF | 4 ± 1 |
| C2 | BIOPROBES, NO AMF | 5 ± 1 |
| C3 | NO BIOPROBES; AMF | 4 ± 1 |
| T1 | BIOPROBES WITH AMF | 91 ± 5 |

Example 3

Temperature Monitoring During Treatment

In a treatment cycle, the bioprobes 110 may be exposed to and become attached to metastatic cells in the treatment area. Pole pieces 304 may be chosen to provide treatment in a selected treatment area, for example, approximately 6 inches in diameter. The patient 105 is typically placed on the treatment bed 106, and the bed controller 108 is typically adjusted to place the targeted tissue at the region of maximum field strength between the poles 304. The pulse width, duty cycle, and peak amplitude of the AMF and the treatment time may be adjusted. Several temperature probes, for example, four temperature probes, may be inserted into the treatment volume. One probe may be located centrally and the other three may be inserted into tissues, within the treatment area that are heated by the AMF. As the tissue heats under the applied AMF, the temperature probes 354 send data to the probe monitor 352. The monitor sends the temperature data via the feedback loop 324 to the RF generator controller 356. Monitoring may be continuous, for example at a data rate of 10 samples per second, and the duty of the RF generator 318 may be adjusted once per second based on individual, 10 sample averages from each probe. If none of the probes 354 sense a temperature greater than the preset limit, the RF generator 318 may be permitted to operate at the original settings. If one or more of the probes 354 senses a temperature over the preset threshold, the controller 356 may send a command to reduce at least one of the duty cycle, the PRF, the magnitude of the magnetic field. This process continues until the treatment is completed.

Example 4

Local Treatment of a Surface Disease

Bioprobes with comprising ligands specific to inflammatory breast cancer are injected into a patient with legions on the chest. After an appropriate circulation time, the patient is exposed to an AMF to inductively heat and kill the cancer cells. The patient is positioned on a non-conductive treatment table 623 and the treatment head 601 is positioned to target the diseased area, as illustrated in FIG. 6b. The treatment head 601 maybe shaped as shown in FIG. 6c and positioned such that the targeted tissue is located as close to the pole faces as possible. A reference to FIG. 6a may be helpful to practice the AMF treatment of this example. The operator enters treatment parameters 611, such as duty, pulse width, treatment time and peak AMF amplitude, and initiates the AMF treatment via the treatment controller 610. The treatment controller 610 starts the RF power supply 605, which excites the resonant network 604 in the treatment head 601, and thereby causing current to flow through the AMF coils 602, producing an AMF in the treatment area. A coolant chiller 607 provides a means for cooling both the RF power supply 605 and the treatment head 601. As the treatment proceeds, patient temperature sensors 617 monitor tissue temperatures to prevent overheating due to excessive eddy currents. Equipment temperature sensors 618 monitor the temperature of critical components and coolant to prevent damage due to overheating. All of the temperature sensors are monitored by the temperature probe controller 616, which digitizes the data and sends it to the treatment controller 610. AMF amplitude sensors 613 monitor the AMF amplitude at various locations to prevent unplanned changes in AMF distribution and send the data to the treatment controller 610. A coolant flow sensor 612 insures that the treatment head 601 is adequately cooled and sends its output to the treatment controller 610. An impedance sensor 614 and frequency sensor 615, each of which provides information about the condition of the AMF coils 602 and matching capacitors 603, can detect the presence of conductive or magnetic materials in or near the treatment area such as, but not limited to pace makers, surgical or dental implants or foreign objects. This data is also sent to the treatment controller 610. The treatment controller 610 records the data from all of the sensors and periodically tests for unsafe conditions, which results in a programmed modification or cessation of the treatment via the master control bus 620.

While the above description of the invention has been presented in terms of a human patient, it will be appreciated that the invention may also be applicable to treating cancers in other mammals.

As noted above, the present invention is applicable to devices for use with magnetic material compositions, and thermotherapeutic methods related thereto. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A device for treating diseased tissue, comprising:
a) a magnetic generator having a core defining at least part of a magnetic circuit, two poles of the magnetic circuit defining a gap therebetween, wherein the poles of the magnetic circuit are shaped to concentrate magnetic flux produced in a portion of a patient containing diseased tissue, a magnetic field passing between two poles, the gap being of sufficient size to receive the portion of the patient containing the diseased tissue, and one or more coils, each comprising one or more coil turns that surround the magnetic circuit; and b) a power supply coupled to provide energy to the magnetic generator so that the magnetic field passing between the two poles alternates at a fundamental frequency of about 1 kHz or more, wherein, the magnetic field is produced by passing electrical current through one or more coil turns.

2. A device according to claim 1, wherein the level of the alternating magnetic field is sufficient to heat the magnetic particles to an effective temperature for treating the diseased tissue.

3. A device according to claim 1, wherein the poles of the magnetic circuit define a gap sufficiently large to receive the patient's chest.

4. A device according to claim 1, wherein the poles of the magnetic circuit are shaped to influence the distribution of flux to maximize the field strength in the treatment area.

5. A device according to claim 1, wherein the poles are canted at an angle to project magnetic flux outward into the treatment area without the patient being placed directly between them.

6. A device according to claim 1, wherein the magnetic circuit comprises i) air, ii) ferrite, iii) powdered iron, iv) laminated magnetic alloy, v) a sputtered laminate, vi) a tape core, vii) magnetic material suspended in a polymer matrix, viii) a liquid suspension of magnetic particles, ix) a paste suspension of magnetic particles, or x) any combination of i-ix.

7. A device according to claim 1, wherein the magnetic circuit has one or more return paths.

8. A device according to claim 1, wherein the fundamental frequency of the alternating magnetic field is in the range of from about 1 kHz to about 1 GHz.

9. A device according to claim 1, wherein the fundamental frequency of the alternating magnetic field is in the range of from about 50 kHz to about 15 MHz.

10. A device according to claim 1, wherein the fundamental frequency of the alternating magnetic field is in the range of from about 100 kHz to about 500 kHz.

11. A device according to claim 1, wherein the alternating magnetic field has a sinusoidal fundamental waveform.

12. A device according to claim 1, wherein the alternating magnetic field has a non-sinusoidal fundamental waveform.

13. A device according to claim 1, wherein the alternating magnetic field has a fundamental waveform that is one of i) square wave, ii) trapezoidal and iii) sawtooth.

14. A device according to claim 1, wherein the alternating magnetic field has a fundamental waveform that is triangular.

15. A device according to claim 1, wherein the alternating magnetic field is amplitude modulated with a pulse width in the range of from about 1 nanosecond to about 600 seconds and a pulse repetition frequency in the range of from about 0.0017 Hz to about 1000 MHz.

16. A device according to claim 1, wherein the alternating magnetic field is modulated with a duty cycle of less than 100%.

17. A device according to claim 1, wherein at least one of the fundamental frequency and the amplitude of the alternating magnetic field is modulated.

18. A device according to claim 16, wherein the alternating magnetic field is amplitude modulated with one of i) sinusoidal modulation, ii) a triangular modulation, iii) a square wave modulation, iv) a trapezoidal modulation and v) a sawtooth modulation, and vi) a combination of any of i)-v).

19. A device according to claim 16, wherein the alternating magnetic field is repetitively modulated having a pulse repetition frequency, the pulse repetition frequency being modulated.

20. A device according to claim 1, wherein the alternating magnetic field between the poles of the magnetic circuit has a strength in the range of from about 10 Oersteds (Oe) to about 10,000 Oe.

21. A device according to claim 1, wherein the alternating magnetic field between the poles of the magnetic circuit has a strength in the range of from about 20 Oe to about 3,000 Oe.

22. A device according to claim 1, wherein the alternating magnetic field between the poles of the magnetic circuit has a strength in the range of from about 100 Oe to about 2,000 Oe.

23. A device according to claim 1, wherein the alternating magnetic field is generated by one or more coils comprising a part of a resonant network.

24. A device according to claim 1, wherein the alternating magnetic field is generated by one or more coils driven by an amplifier.

25. A device according to claim 1, wherein the alternating magnetic field is generated by one or more coils driven by one or more pairs of pulse forming networks.

26. A device according to claim 1, wherein the alternating magnetic field has a DC offset to attract the magnetic material to the treatment area.

27. A device according to claim 1, further comprising a detector to monitor a physical characteristic of the portion of the patient being treated, and a feedback circuit to control the power supply in response to the monitored physical characteristic.

28. A device according to claim 27, wherein the detector is one of a temperature monitor, an impedance monitor, and a magnetic field amplitude monitor.

29. A device according to claim 1, wherein the one or more coils are combined with capacitors in series to form a resonant circuit.

30. A device according to claim 27, wherein the resonant circuit impedance is monitored to detect the presence of magnetic or conductive materials in the treatment area.

31. A device according to claim 27, wherein the resonant frequency is monitored to detect the presence of magnetic or conductive materials in the treatment area.

32. A device according to claim 27, wherein the magnetic field strength is monitored at one or more locations to detect any local perturbations caused by magnetic or conductive materials in or near the treatment area.

33. A device according to claim 1, wherein the poles of the magnetic circuit are formed from pole pieces, the pole pieces being in an adjustable relationship with each other so that the size of the gap is adjustable.

34. A device according to claim 1, wherein the poles of the magnetic circuit are formed from removable pole pieces of selected shape.

35. A device according to claim 1, wherein the magnetic generator is liquid cooled.

36. A device according to claim 1, wherein the one or more coil turns are in series.

37. A device according to claim 1, wherein the location of one or more coil turns relative to the gap maximizes the flux density in the gap, for a given coil current.

38. A device according to claim 1, wherein the location of one or more coil turns relative to the gap minimizes the electrical insulation necessary to insure patient safety.

39. A device according to claim 1, further comprising one or more helper coils operated in phase with the main coils.

40. A device according to claim 39, wherein the helper coils are in series or in parallel with the main coils and are operated with or without a delay line.

41. A device according to claim 1, wherein the one or more coil turns have decreasing diameter causing the coil interior to have a conical shape.

42. A device according to claim 1, wherein the one or more coils comprises a single-turn of a conical shape, and wherein each single-turn is associated with at least one end of the magnetic circuit.

43. A device according to claim 1, wherein the one or more coils turns comprise surface details, and wherein the surface details increase surface area of the coil.

44. A device according to claim 1, wherein the coils are cooled to enhance conductivity.

45. A device according to claim 1, wherein the magnetic field is generated by rotating permanent magnets.

46. A device according to claim 1, wherein the magnetic field is generated by rotating one or more pairs of permanent magnets, with each pair having a return path comprised of air, a magnetic material, or a combination of the two.

47. A device according to claim 1, wherein the magnetic field is generated by rotating multiple pairs of permanent magnets with each pair having a return path comprised of air, a magnetic material, or a combination of the two.

48. A device according to claim 1, further comprising a thermoplastic mask to aid targeting.

49. A method for treating diseased tissue in a patient, comprising:
   a) administering to a patient a magnetic material composition that comprises at least one magnetic particle attached to a diseased cell specific ligand; and
   b) applying an alternating magnetic field to a region of the patient containing diseased cells such that the magnetic material composition inductively heats, wherein the alternating magnetic field is applied using a device that comprises: i. a magnetic generator having a magnetic circuit defining at least part of a magnetic circuit, two poles of the magnetic circuit defining a gap therebetween, wherein the poles of the magnetic circuit are shaped to concentrate magnetic flux produced in the region of the patient containing diseased cells, a magnetic field passing between two poles, the gap being of sufficient size to receive a portion of the patient containing the diseased cells, and one or more coils, each comprising one or more coil turns that surround the magnetic circuit; and ii. a power supply coupled to provide energy to the magnetic generator so that the magnetic field passing between the two poles has a strength is in the range of from about 10 Oe to about 10,000 Oe, and alternates at a frequency in the range of from about 1 kHz to 1 GHz, wherein, the magnetic field is produced by passing electrical current through the one or more coil turns, and wherein the magnetic circuit comprises i) air, ii) ferrite, iii) powdered iron, iv) laminated magnetic alloy, v) a sputtered laminate, vi) a tape core, vii) magnetic material suspended in a polymer matrix, viii) a liquid suspension of magnetic particles, ix) a paste suspension of magnetic particles, or x) any combination of i-ix.

50. A method according to claim 49, wherein the strength of the alternating magnetic field is sufficient to heat the magnetic particles to an effective temperature for treating the diseased tissue.

51. A method according to claim 49, wherein the poles of the magnetic circuit are shaped to influence the distribution of flux to maximize the field strength in the treatment area.

52. A method according to claim 49, wherein the poles of the magnetic circuit are canted at an angle to project magnetic flux outward into the treatment area without the patient being placed directly between them.

53. A method according to claim 49, wherein the magnetic circuit has one or more return paths.

54. A method according to claim 49, wherein the fundamental frequency of the alternating magnetic field is in the range of from about 100 kHz to about 500 kHz.

55. A method according to claim 49, wherein the alternating magnetic field has a sinusoidal fundamental waveform.

56. A method according to claim 49, wherein the alternating magnetic field has a non-sinusoidal fundamental waveform.

57. A method according to claim 49, wherein the alternating magnetic field has a fundamental waveform that is one of i) square wave, ii) trapezoidal and iii) sawtooth.

58. A method according to claim 49, wherein the alternating magnetic field is amplitude modulated with one of i) sinusoidal modulation, ii) a triangular modulation, iii) a square wave modulation, iv) a trapezoidal modulation and v) a sawtooth modulation, and vi) a combination of any of i)-v).

59. A method according to claim 49, wherein at least one of the fundamental frequency and the amplitude of the alternating magnetic field is modulated.

60. A method according to claim 49, wherein the alternating magnetic field is repetitively modulated having a pulse repetition frequency, the pulse repetition frequency being modulated.

61. A method according to claim 49, wherein the alternating magnetic field is generated by the one or more coils comprising a part of a resonant network.

62. A method according to claim 49, wherein the alternating magnetic field is generated by the one or more coils driven by an amplifier.

63. A method according to claim 49, wherein the alternating magnetic field is generated by the one or more coils driven by one or more pairs of pulse forming networks.

64. A method according to claim 49, further comprising monitoring of the amplitude of the magnetic field, wherein the monitoring result is used to modify or curtail the treatment.

65. A method according to claim 49, wherein the coils are combined with capacitors in series, in parallel, or a combination of series and parallel to form a resonant circuit.

66. A method according to claim 65, wherein the resonant circuit impedance is monitored to detect the presence of magnetic or conductive materials in or near the treatment area.

67. A method according to claim 65, wherein the resonant frequency is monitored to detect the presence of magnetic or conductive materials in or near the treatment area.

68. A method according to claim 49, wherein the magnetic field strength is monitored at one or more locations to detect any local perturbations caused by magnetic or conductive materials in or near the treatment area.

69. A method according to claim 49, wherein the poles of the magnetic circuit are formed from pole pieces, the pole pieces being in an adjustable relationship with each other so that the size of the gap is adjustable.

70. A method according to claim 49, wherein the poles of the magnetic circuit are formed from removable pole pieces of selected shape.

71. A method according to claim 49, wherein the magnetic generator is liquid cooled.

72. A method according to claim 49, wherein the one or more coil turns are configured in series.

73. A method according to claim 49, wherein the one or more coil turns are located in a position relative to the gap so as to maximize the flux density in the gap, for a given coil current.

74. A method according to claim 49, wherein the one or more coil turns are located in a position relative to the gap so as to minimize the electrical insulation necessary to insure patient safety.

75. A method according to claim 49, wherein the coil turns have decreasing diameter causing the coil interior to have a conical shape.

76. A method according to claim 49, wherein the one or more coil turns comprise surface details, and wherein the surface details increase surface area of the coil.

77. A method according to claim 49, wherein one or more helper coils are located near the gap and operated in phase with the main coils.

78. A method according to claim 77, wherein the helper coils are configured in series or in parallel with the main coils, and wherein the helper coils are operated with or without a delay line.

79. A method according to claim 49, wherein a single-turn coil having a conical shape is used at each end of the magnetic circuit.

80. A method according to claim 49, wherein the one or more coils are cooled.

81. A method according to claim 49, further comprising targeting the region of the patient containing diseased cells utilizing a thermoplastic mask.

82. A method for treating diseased tissue, comprising:
iteratively adjusting one or more parameters of a treatment simulation to determine optimal parameters for the treatment of diseased tissue in a patient, wherein the heating of the diseased tissue is maximized while the eddy current heating of healthy tissue in the patient is minimized;
administering to the patient a magnetic material composition that comprises at least one magnetic particle; and
heating the magnetic material composition under the optimal parameters such that the magnetic material composition inductively heats the diseased tissue in the patient.

83. A method according to claim 82, wherein the one or more adjusted parameters is fundamental frequency, coil current, pulse shape, pulse repetition envelope, pulse repetition frequency, duration, duty cycle, magnet position, or any combination thereof.

84. A method according to claim 49, wherein the method is used in the treatment of cancer, diseases of the immune system, pathogen-borne diseases, hormone-related diseases, and undesirable matter, such as toxins, reaction-by-products associated with organ transplants, and other abnormal cell or tissue growth.

85. A device according to claim 1, wherein the one or more coils are combined with capacitors in parallel to form a resonant circuit.

86. A device according to claim 1, wherein the one or more coils are combined with capacitors in a combination of series and parallel to form a resonant circuit.

87. A device according to claim 1, wherein the one or more coil turns are in parallel.

88. A device according to claim 1, wherein the one or more coil turns are in a combination of series and parallel.

89. A method according to claim 49, wherein the one or more coil turns are configured in parallel.

90. A method according to claim 49, wherein the one or more coil turns are configured in a combination of series and parallel.

91. A device according to claim 27, wherein the resonant circuit impedance is monitored to detect the presence of magnetic or conductive materials outside of the treatment area.

92. A device according to claim 27, wherein the resonant frequency is monitored to detect the presence of magnetic or conductive materials outside of the treatment area.

* * * * *